United States Patent [19]
Schmitz

[11] Patent Number: 5,779,831
[45] Date of Patent: Jul. 14, 1998

[54] METHOD AND APPARATUS FOR MAKING AN UNDERGARMENT HAVING OVERLAPPING OR BUTT-TYPE SIDE SEAMS

[75] Inventor: Christoph Johann Schmitz. Euskirchen-Stotzheim, Germany

[73] Assignee: The Procter & Gamble Company. Cincinnati, Ohio

[21] Appl. No.: 849,938

[22] PCT Filed: Dec. 8, 1995

[86] PCT No.: PCT/US95/16152

§ 371 Date: Jun. 20, 1997

§ 102(e) Date: Jun. 20, 1997

[87] PCT Pub. No.: WO96/20076

PCT Pub. Date: Jul. 4, 1996

[30] Foreign Application Priority Data

Dec. 24, 1994 [EP] European Pat. Off. ............. 94120638

[51] Int. Cl.$^6$ .................. A41B 9/12; A61F 13/15; B32B 31/04; B32B 31/20

[52] U.S. Cl. ................ 156/73.1; 2/402; 156/163; 156/164; 156/217; 156/226; 156/227; 156/264; 156/269; 156/308.4; 156/443; 156/538; 156/539; 156/543; 156/566; 156/580.1; 604/396

[58] Field of Search .................. 156/73.1, 163, 156/164, 217, 222, 226, 227, 264, 269, 292, 308.4, 443, 510, 516, 522, 538, 539, 543, 544, 552, 556, 562, 566, 567, 568, 580.1; 2/402, 403, 406; 604/396

[56] References Cited

U.S. PATENT DOCUMENTS 3,604,015  9/1971  Dove ........................... 156/227 X
5,626,711  5/1997  Herrmann ...................... 156/538 X

*Primary Examiner*—Adrienne C. Johnstone
*Attorney, Agent, or Firm*—Theodore P. Cummings; Steven W. Miller; Jacobus C. Rasser

[57] ABSTRACT

A method for forming an undergarment comprises the steps of transporting a two-dimensional web in a substantially flattened position on a transport device, cutting the web along a transverse edge to form a two-dimensional pre-form, gripping the pre-form adjacent each waist section with a gripping device in four gripping areas, jointly rotating at least the gripping means which hold the gripping areas in the region of the first transverse edge of the pre-form around a first axis of rotation extending substantially parallel to the transverse edges of the pre-form, rotating each gripping device around a respective axis of rotation extending generally parallel to the longitudinal sides of the pre-form to place the sealing areas located along the same longitudinal side in a contacting relationship, joining the superimposed sealing areas in a sealing unit, and releasing the undergarment from the gripping device. The apparatus comprises an umbrella-type mechanism.

27 Claims, 20 Drawing Sheets

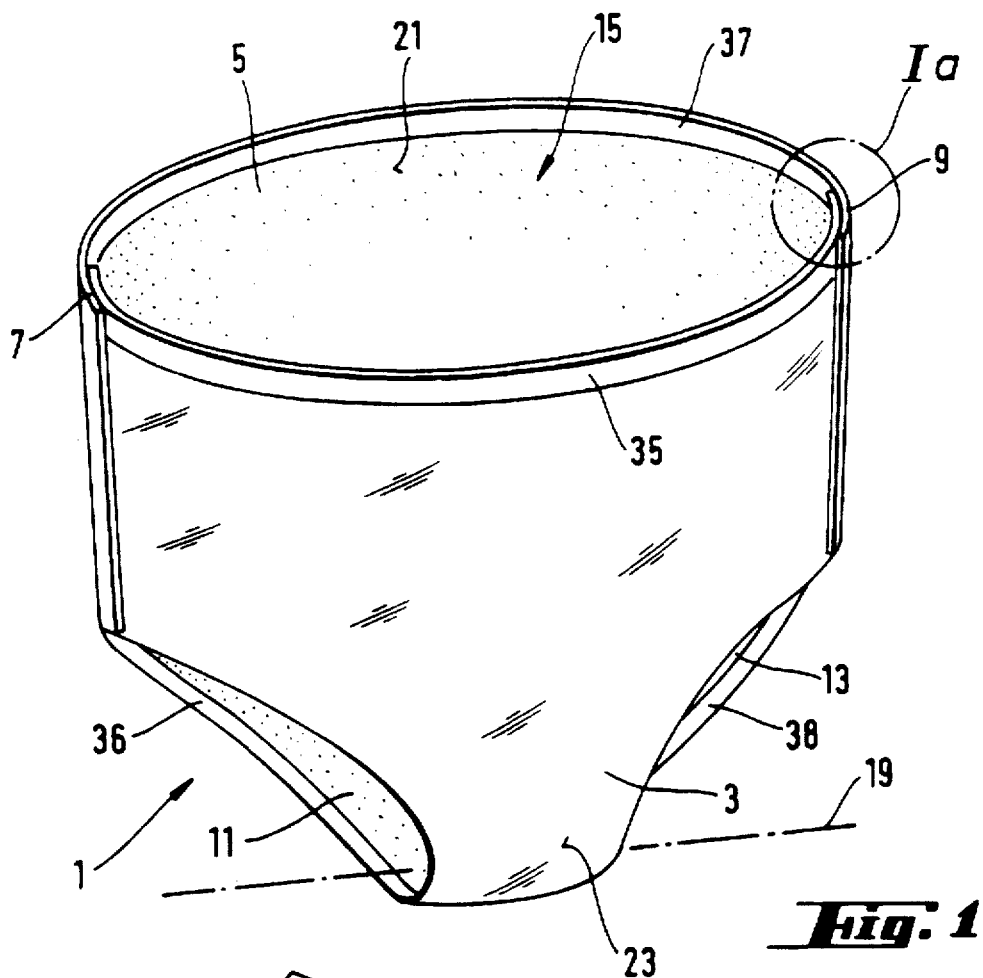
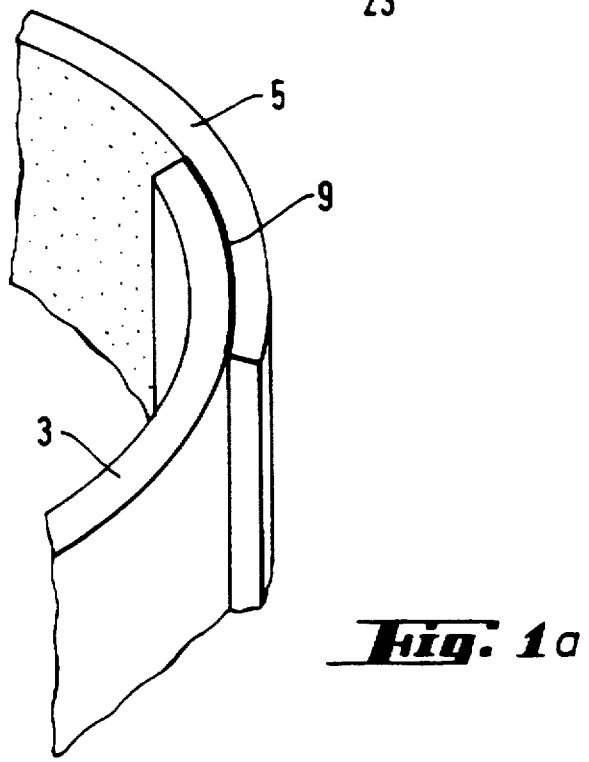

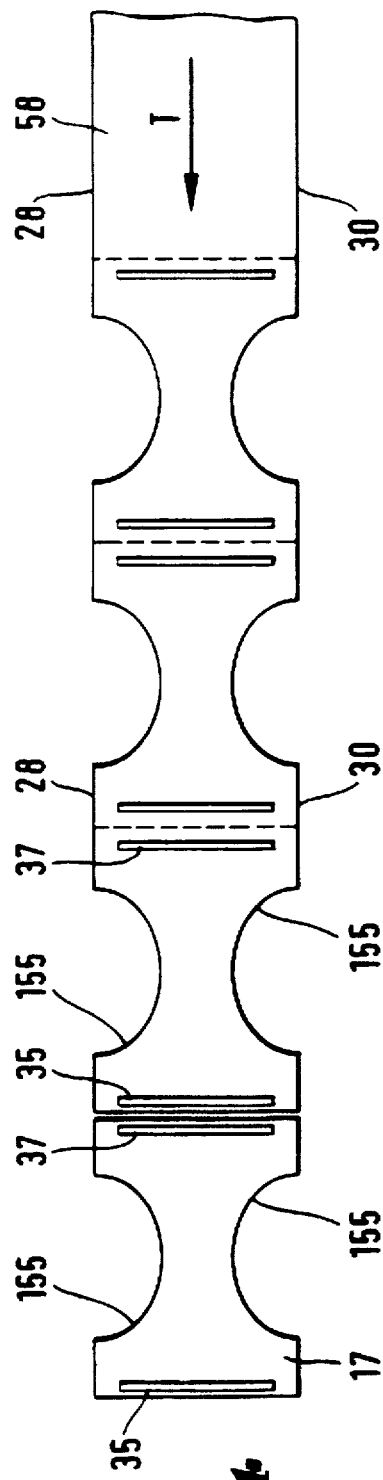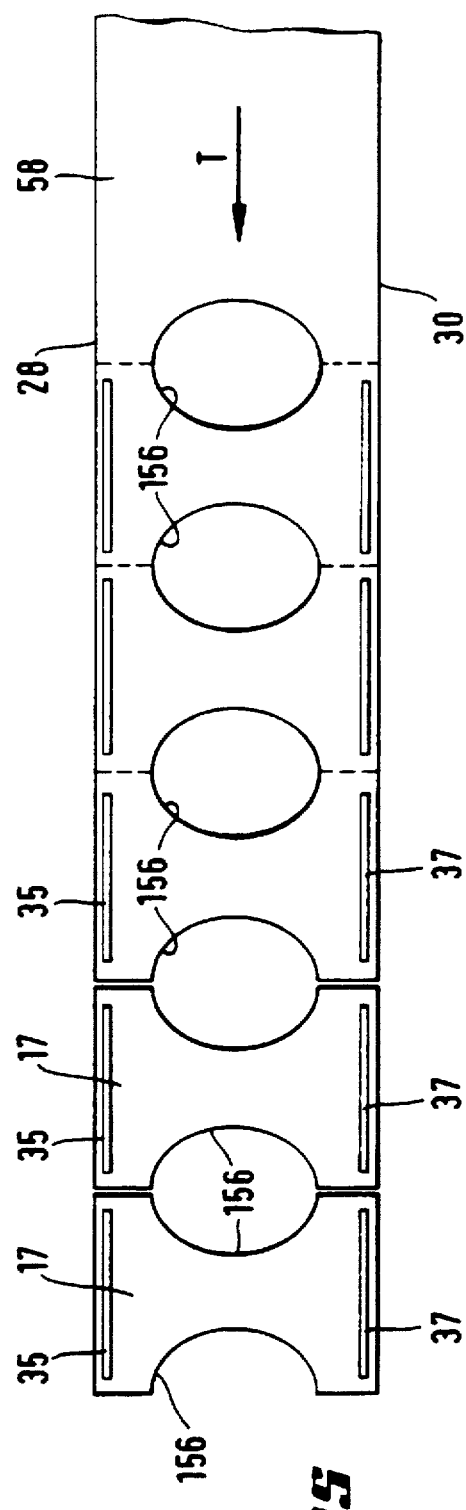

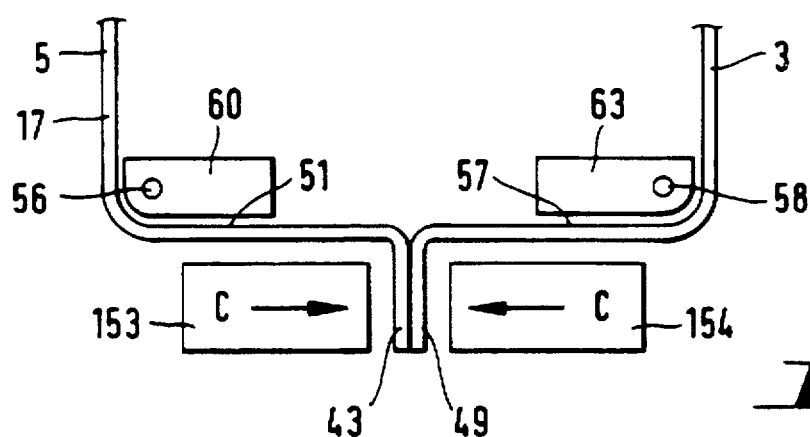
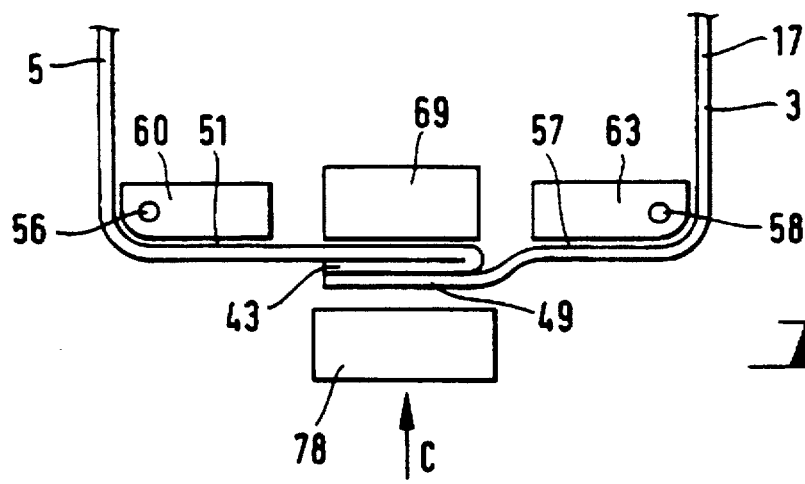
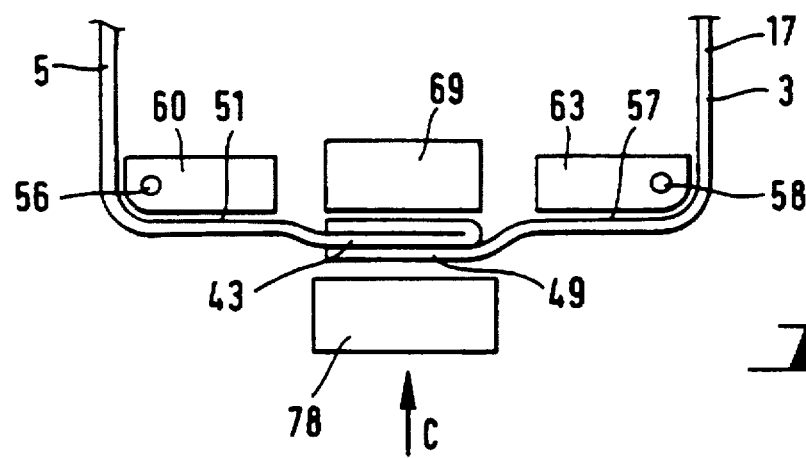

METHOD AND APPARATUS FOR MAKING AN UNDERGARMENT HAVING OVERLAPPING OR BUTT-TYPE SIDE SEAMS

FIELD OF THE INVENTION

The invention relates to a method of making an undergarment having side seams from a substantially two-dimensional web, the web having two longitudinal sides and a first transverse edge extending transversely to the longitudinal sides.

BACKGROUND OF THE INVENTION

From EP-A-0 187 728 (Heran) a disposable absorbent article is known having manually tearable side seams. The seams may be butt-type seams or overlapping side seams.

WO 93/09742 describes an absorbent article having overlapping ultrasonically-bonded side seams.

It is an object of the present invention to provide a method for producing an undergarment, in particular an absorbent article, having strong side seams, wherein the sealing areas can be accurately positioned in a sealing configuration in a reproducible manner.

It is another object of the present invention to provide a method for producing an undergarment, in particular a disposable absorbent article, having side seams which can be easily manually separated.

It is a further object of the invention to provide a method for producing an undergarment having aesthetically looking side seams while producing little trim and operating at high speeds.

It is another object of the invention to provide a method for producing an undergarment having an elasticized waist providing accurate process control and small variability in the placement of the side seams.

It is a further method to provide an apparatus for carrying out the above method, which apparatus is of relatively simple construction, and allows high-speed formation of the side seams.

SUMMARY OF THE INVENTION

The method according to the invention comprises the steps of:

transporting the web in a substantially flattened position on a transport means along a transport trajectory, cutting the web along a second transverse edge to form a two-dimensional pre-form, the pre-form comprising the first and the second transverse edge of the web and two longitudinal edges, each longitudinal edge having two waist sections and a crotch section located intermediate the waist sections, a sealing area being located adjacent and inboard of each waist section, gripping the pre-form adjacent each waist section with gripping means in four gripping areas, the gripping areas being located near each sealing area, jointly rotating at least the gripping means which hold the gripping areas in the region of the first transverse edge around a first axis of rotation extending substantially parallel to the transverse edges of the pre-form to place the first transverse edge generally parallel and opposite to the second transverse edge, superimposing the sealing areas which are located along the same longitudinal side in a contacting relationship, joining the superimposed sealing areas in a sealing means, thus forming the absorbent article, and releasing the absorbent article from the gripping means.

The method according to the invention doubles over the pre-form along its transverse center line and accurately places the sealing areas of the pre-form in a superimposed relationship. The method involves a controlled handover of the pre-form from the transport means to a folding-and-sealing unit, wherein the position of each sealing area during all phases of the transport step and the handover step is clearly defined. This allows for high speed formation of the undergarment's side seams with little process variability. This is especially important in case the transverse edges of the pre-form are elasticated and therefore need to be confined to a stretched state in all phases of the transport- and sealing process.

The seams that are formed can be butt-type seams, which are made by superimposing the sealing areas in the region of the first waist sections with their interior sides onto the interior sides of the sealing areas in the region of the second waist sections. For the butt-type side seams, the sealing areas in the region of each waist section are located on the same side of the pre-form.

In a preferred embodiment of the method according to the invention, the step of superimposing the sealing areas comprises rotating each gripping means around a respective axis of rotation extending generally parallel to the longitudinal sides of the pre-form to place the sealing areas which are located along the same longitudinal side in an overlapping relationship, to form overlapping side seams. In the overlapping side seams the sealing areas in the region of the first waist section are located on a different side of the pre-form than the sealing areas in the region of the second waist sections.

By consecutively rotating the ears of the absorbent article perpendicularly to the plane of the pre-form, the sealing areas are made to overlap and can be contacted for instance by an ultrasonic sealing unit to attach the overlapping sealing areas. Overlapping side seams are located in the plane of the side panels of the finished undergarment. Hence the seams are of pleasing aesthetics and are wearer-friendly. Furthermore, in case the undergarment is formed by a disposable absorbent article, the overlapping side seams have a high shear strength but can easily be manually detached for disposal of the absorbent article. The overlapping seams may alternatively be connected by mechanical fasteners, such as Velcro® hook-type and loop-type materials or by means of adhesive tapes. Such re-fastenable seams can be undone by the user without ripping the article and can be reclosed for further use.

The longitudinal sides of the pre-form are preferably parallel to the length-direction of the web, such that each preform has the same width as the width of the web. Alternatively, the longitudinal sides of the preforms are formed by the transverse side of the web, such that the preforms are transported with their longitudinal sides perpendicular to the direction of transport.

The web from which the absorbent article is formed comprises a flexible material, which may be a woven fabric, a non-woven material, a thermoplastic film or any combination or laminate thereof. The undergarment formed by the method according to the invention can be re-usable and may be used in combination with disposable absorbent inserts. Such inserts may comprise a liquid-pervious topsheet, a liquid-impervious backsheet and an absorbent core interposed therebetween.

An embodiment of the method according to the invention comprises the steps of forming the web by combining a liquid-impervious backsheet, an absorbent core and a liquid-pervious topsheet, such that the finished undergarment after formation of the side seams is a disposable absorbent article of the pull-on type. Disposable absorbent articles of the pull-on type are characterized by having pre-formed side seams instead of the usual mechanical or adhesive tape fasteners.

The web from which the undergarment is formed may be of elastic or elasticated material, such that the web is elastically extensible. If the web is of substantially non-elastic material, the method according to the invention comprises a length compensating step. In the length-compensating step, at least the first axis of rotation is displaced to prevent stretching the pre-form in the direction of the longitudinal edge, when the pre-form is doubled-over along its transverse center line.

When overlapping side seams are formed, a width-compensating step in the direction of the transverse edge may be carried out. In this step, the distance between the gripping areas located in the region of the same transverse edge is decreased. This prevents stretching of the pre-form in the direction of the transverse edges when the gripping means are rotated around their gripper axes.

The need for length or width compensation of the pre-form, depends on the way the pre-from is folded. If the pre-form is folded around an axis which is located on the concave side of the fold, a length-compensation step is required. If the pre-form is folded around an axis which is located on the convex side of the fold, the pre-form material is gathered by the folding and no length compensation is necessary.

In an embodiment of the method according to the invention, the gripping means, after gripping the article, are rotated around a main axis which extends generally transversely to the longitudinal sides of the web towards a stationary or rotating sealing unit. In this embodiment the gripping means are rotated towards and away from the transport trajectory of the web. In this way a number of gripping means can be placed onto the main axis and can consecutively be rotated towards and away from the transport means carrying the web, such that high speed sealing of the pre-forms is effected.

Preferably the gripping means are rotated tangentially to the transport trajectory at a velocity which is substantially equal to the speed of transport of the web along the transport trajectory. Hereby the relative velocity between the gripping means and the web is made substantially zero such that handover from the transport means onto the gripping means can take place at a continuous speed of transport of the web.

An apparatus for carrying out the method according to the invention comprises at least one folding-and-sealing unit, which folding-and-sealing unit has:

a first and second carrier arm, each carrier arm being hingingly mounted on a hinging axis, the hinging axes extending generally transversely to the carrier arms, gripping means attached to each carrier arm for gripping the absorbent article in four gripping areas, carrier arm-actuating means for rotating at least one carrier arm around its hinging axis to a sealing position and sealing means for contacting the article in the sealing areas when the carrier arms and gripping means are in the sealing position.

In a preferred embodiment, each carrier arm is in one point attached to a connecting arm. Each connecting arm is in on one end attached to a hinge point that is comprised in a lower member which is displaceable relative to the hinging axes of the carrier arms, along a center line. The center line is located midway between the hinging axes and extends generally transversely or perpendicular to the hinging axes. In this manner an "umbrella type" construction is formed. This construction is relatively simple and accurately operates at high speeds. By varying the distance between the hinging axes on which the carrier arms are suspended and the hinging points of the connecting arms, the opposed carrier arms are moved outwardly and inwardly respectively. The umbrella-type mechanism allows accurate alignment of the sealing areas in a simple and reproducible manner.

Each gripping means may be rotatable around a respective gripper axis which is positioned generally parallel to the carrier arms, the apparatus comprising gripper actuating means for rotating each gripping means around the gripper axes to a sealing position. By rotation of the gripping means around the gripper axes, overlapping side seams are produced. The actuating means for rotation of the grippers may be formed by a contacting element which engages with the gripping means upon rotation of the carrier arms and which guides the grippers to rotate around their gripper axes, or by other actuators, such as cans, springs or wires.

In a further embodiment of the apparatus according to the invention, each carrier arm is connected with its hinging axis to a first end of a respective pivot member, the second end of each pivot member being rotatably connected to a central pivot axis located on the center line and extending generally parallel to the hinging axes. By rotation of the pivot members around the centered pivot axis a length-compensation takes place which prevents deformation of non-elastically extensible webs.

Another embodiment of an apparatus according to the invention comprises two distance-control arms, each distance-control arm being with one end hingingly connected to a respective connecting arm and being with another end hingingly connected to a respective hinge point in the region of a center line.

The distance control arms in cooperation with the connecting arms impart a unique position to each gripping means throughout the whole gripping and sealing cycle, for each position of the connecting arms.

In a preferred embodiment, the gripping means are formed by vacuum grippers, comprising a perforated surface across which a pressure differential is maintained. Such grippers can easily engage in a non-damaging manner with the web and can quickly be disengaged by switching off the vacuum and by venting the grippers.

BRIEF DESCRIPTION OF THE DRAWINGS

Embodiments of the method and apparatus in accordance with the invention will be described in detail with reference to the accompanying drawings. In the drawings:

FIGS. 1 and 2 show embodiments of an undergarment having overlapping and butt-type side seams respectively.

FIGS. 24 and 25 show a schematic top plan view of a web from which the pre-forms are cut in a length-wise and in a cross-wise direction respectively.

FIG. 26 shows a schematic top view of the gripping and sealing means on formation of a butt-type side seam.

FIG. 27 shows a schematic top view of the gripping and sealing means on formation of a combined overlapping and butt-type side seam, and FIG. 28 shows a schematic top view of the gripping and sealing means on formation of a three-layer overlapping side seam.

DETAILED DESCRIPTION OF THE INVENTION

Figure 2:
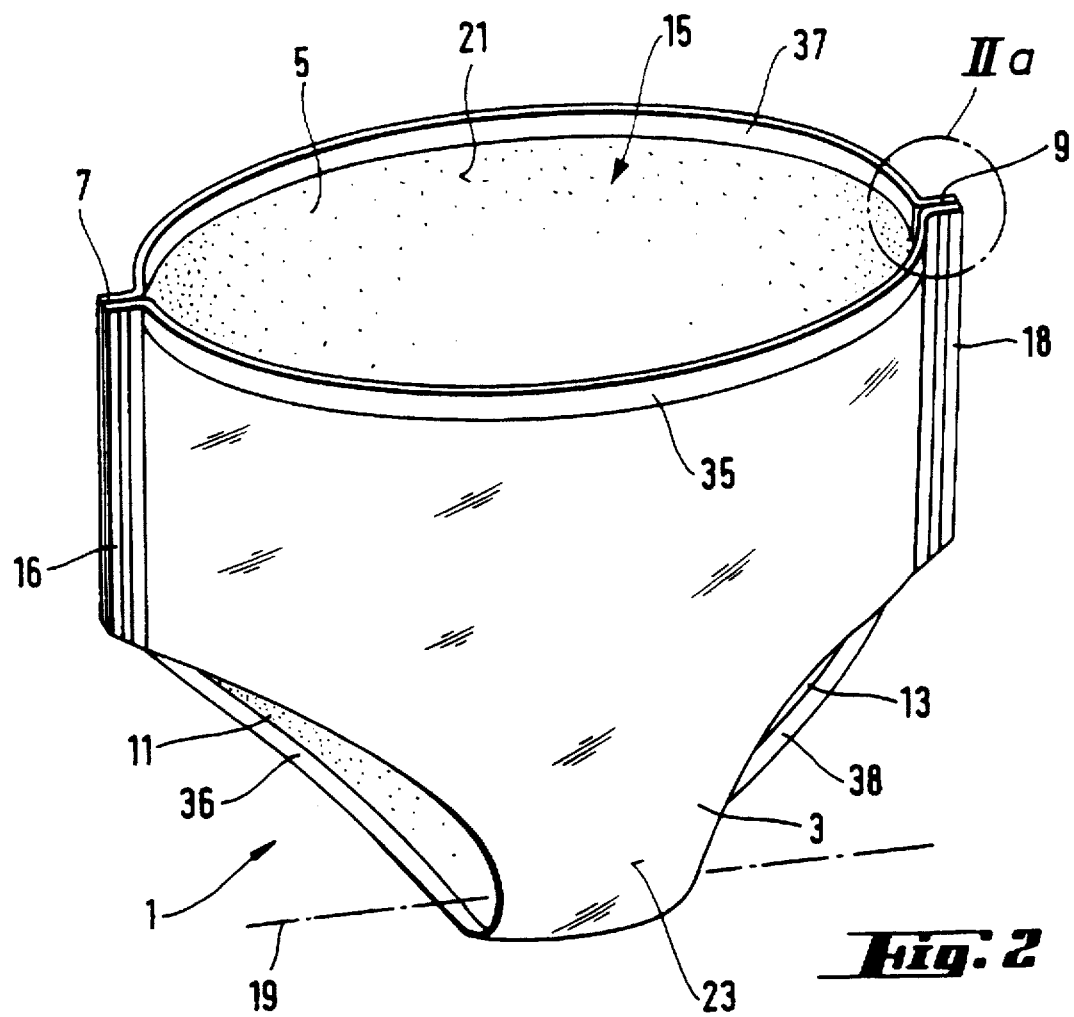
Figure 2A:
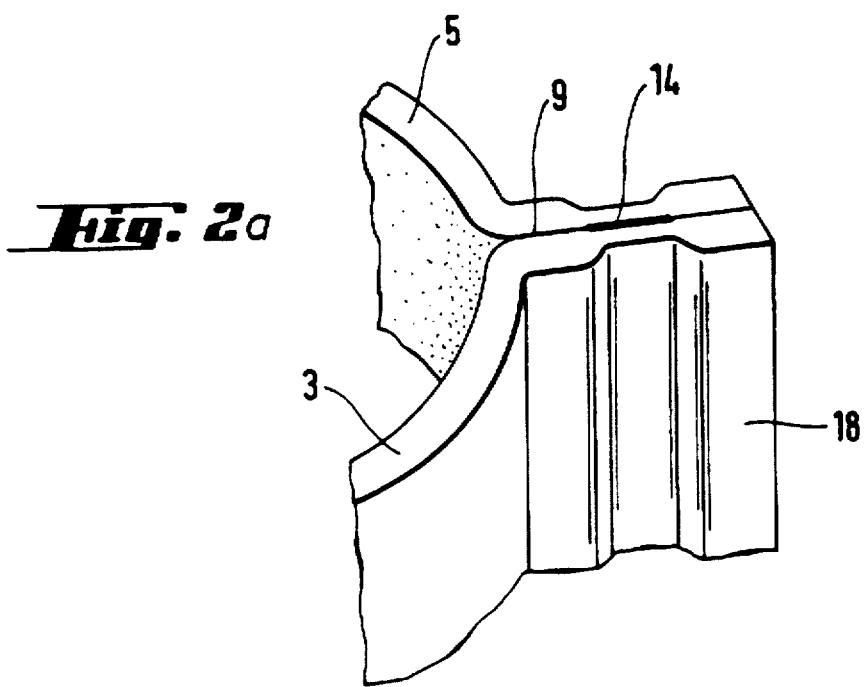

FIG. 1 shows a finished undergarment 1, in particular a disposable absorbent article of the pull-on type having a front panel 3 and a back panel 5. The front panel and the back panel are joined together at the area of overlapping side seams 7, 9 to form a three dimensional disposable garment having leg openings 11, 13 and a waist opening 15. The side seams 7,9 are formed by overlapping parts of the front panel 3 and the back panel 5. Overlapping side seams have favorable characteristics with respect to shear strength (in the plane of the front and back panels) and can, in case the undergarment is a disposable absorbent article, be easily torn apart for removal of a used article from the wearer.

Alternatively, the overlapping side seams may be joined by Velcro-type side seams comprising patches of hook-type and loop-type material. These patches may be located parallel to the sides seams 7,9 or may be located perpendicular to the seams 7,9. Alternatively, the side seams may be joined by adhesive tape taps extending perpendicularly to the seams 7,9. The Velcro®-type sealing means or adhesive tape sealing means are attached by the manufacturer to form the three dimensional garment. After the garment has been attached on a wearer, the seams 7,9 can be unfastened for inspection of the inside of the article and can after inspection be re-closed by the user for further use.

The waist opening 15 and the leg openings 11,13 are elasticated so that they contract and snugly fit around the waist and legs of the wearer to provide gasketing seals which prevent liquids of leaking from the garment 1.

FIG. 2 shows an undergarment 1 having outwardly located butt-type seams 16, 18. The butt-type seams 16, 18 are made by folding the pre-form, or blank, from which the article 1 is formed along its transverse center line 19 and superimposing the sealing areas that are located on the same surface of the blank in a face-to-face relationship. The seams may be formed by pressure bonding, ultrasonic bonding, heat sealing adhesive attachment, or mechanical attachment.

The sealing line 14 of the butt-type seam is preferably located inboard from the outer periphery and leaves the outer edges of the seam unattached in order to maintain a soft edge.

The butt-type side seams 16 and 18 may be located on the inside of the undergarment 1. Inner seams can be obtained when the pre-form, or blank, of the undergarment is folded along its transverse center line 19 so that its inner surface if facing outwardly upon formation of the seams. Subsequently, by an inverting step, the seams 16 and 18 are turned inwardly.

The undergarment 1 as shown in FIGS. 1 and 2 can comprise a single layer or multiple layers of woven or non-woven material, and may comprise a thermoplastic film. The undergarment may form a re-usable diaper holder which is to be used in combination with a disposable absorbent insert core. Preferably, the undergarment forms a unitary disposable absorbent article, in which a liquid-impermeable backsheet, an absorbent core and a liquid permeable topsheet are combined to form an integral structure.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. The present invention is also applicable to other absorbent articles such as incontinent briefs, incontinent undergarments, diaper holders and liners, feminine hygiene garments, and the like.

Figure 3:
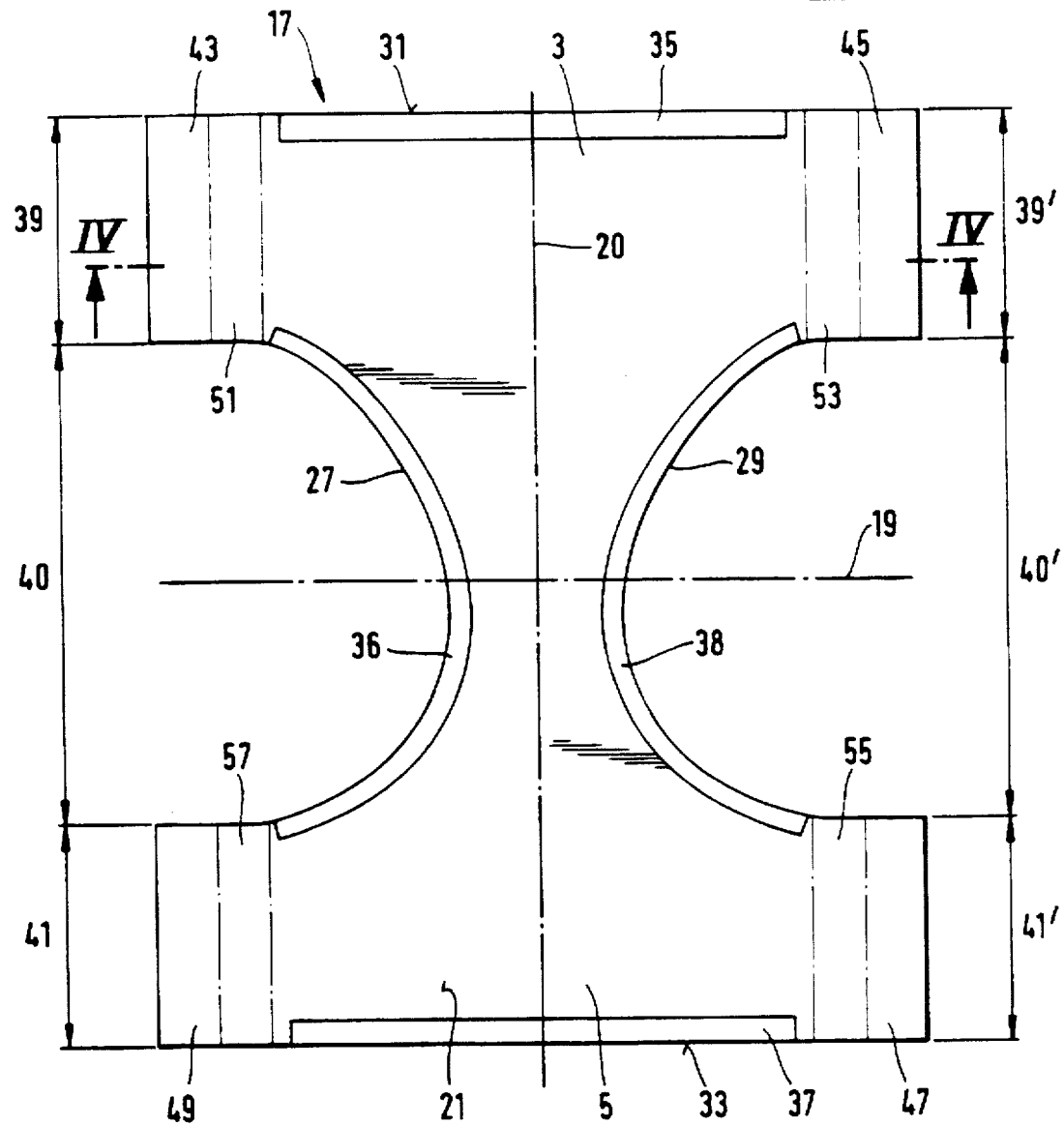
FIG. 3 shows a top plan view of a two-dimensional pre-form for forming an absorbent article having side seams.
Figure 4:
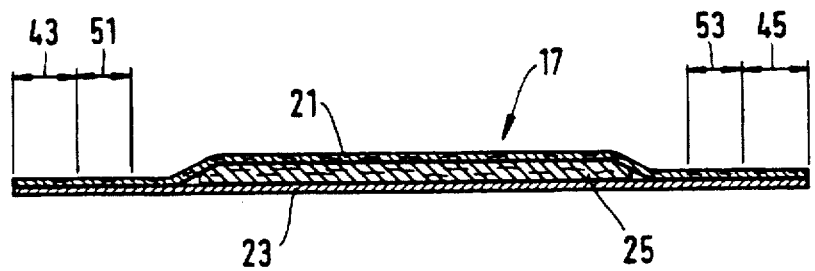
FIG. 4 shows a cross-sectional view of the article of FIG. 3 along line I—I.

FIG. 3 shows the pre-form 17, which will be further referred to as "blank" 17, for forming an absorbent article having side seams. FIG. 4 show a cross-sectional view of the blank 17 along the line I—I of FIG. 3. The blank 17 comprises a liquid-pervious topsheet 21, a liquid-impervious backsheet 23 and an absorbent core 25 interposed between the topsheet and the backsheet. The blank 17 comprises two longitudinal edges 27,29 and two transverse edges 31,33. The longitudinal edges 27,29 and the transverse edges 31,33 form the periphery of the blank 17. The longitudinal edges 27,29 extend generally in the direction of the longitudinal center line 20 and comprise cut-out regions which are to form the leg openings 11,13 of the absorbent article in its assembled state. The blank 17 comprises waist elastics 35,37 and leg elastics 36,38. Each longitudinal edge 27,29 comprises a first waist section 39,39' and a second waist section 41,41'. The waist sections 39,39' and 41,41' of the longitudinal edges 27,29 are located on both sides of a central crotch section 40,40' of each edge 27,29. Each waist section comprises a sealing area 43,45,47,49. A gripping area 51,53, 55,57 is located adjacent each sealing area 43,45,47,49.

Figure 5:
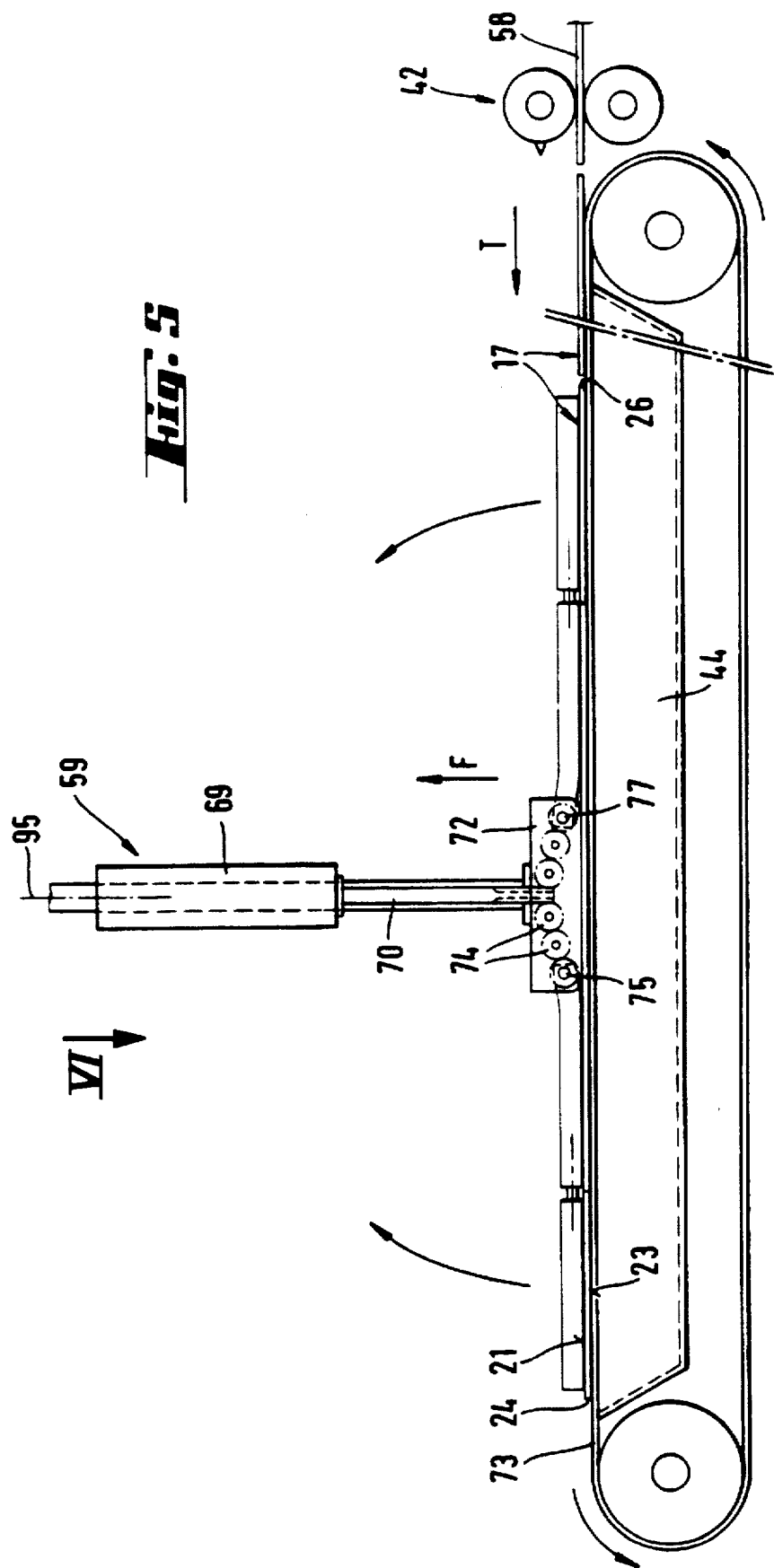
FIG. 5 shows a schematic side elevational view of a folding-and-sealing unit according to the invention in the gripping position.
Figure 6:
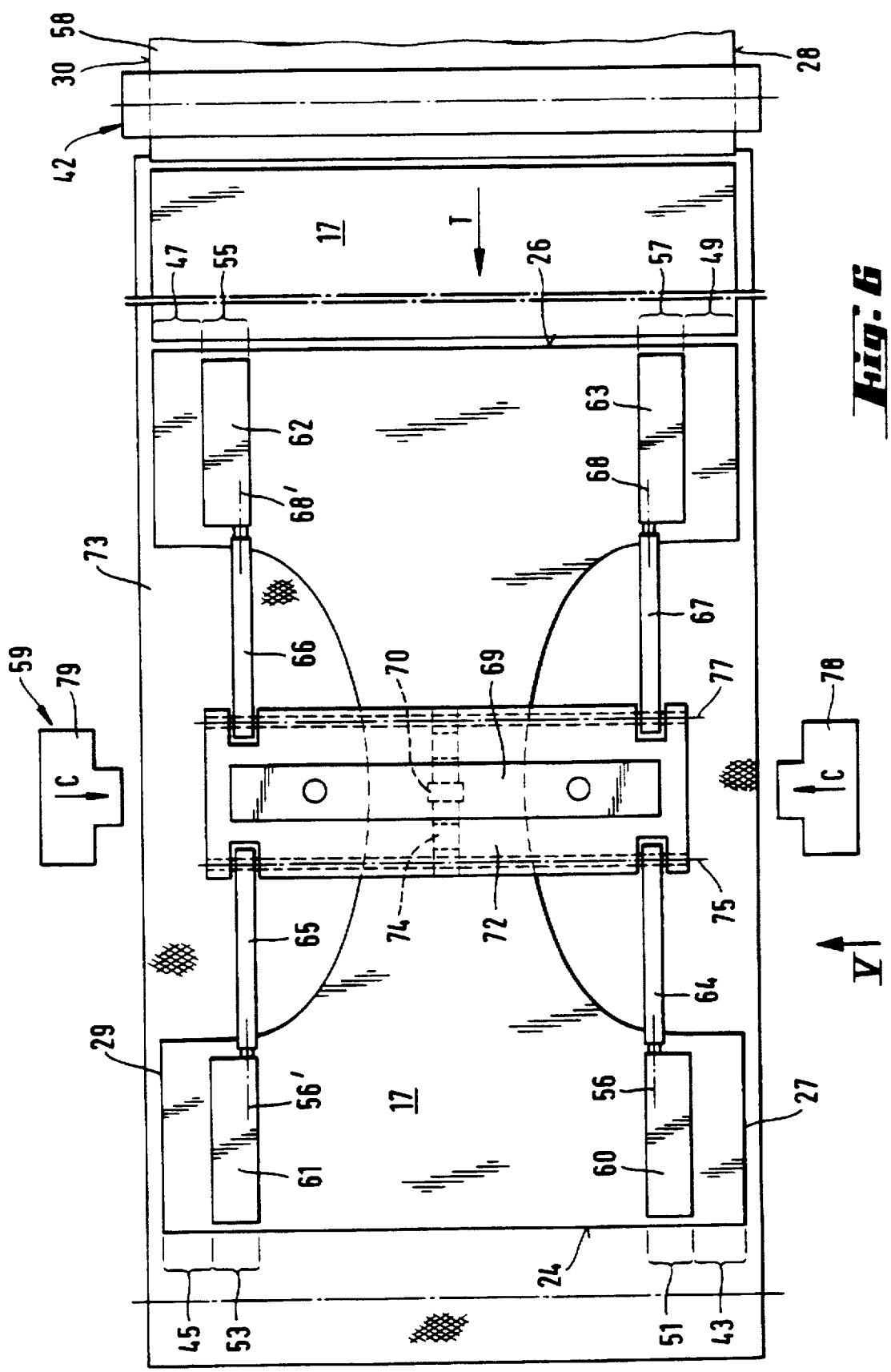
FIG. 6 shows a top elevational view of the apparatus of FIG. 5.

FIG. 5 shows a schematic side elevational view of the apparatus for forming an absorbent article having side seams according to the invention. FIG. 6 shows a top elevational view of the apparatus of FIG. 5. A continuous web 58 is transported in a substantially flattened state along a transport trajectory on a conveyor belt 73 in a direction of transport T. A cutting means 42 cuts the web transversely across its width to from individual blanks 17. The blanks 17 are transported in their substantially flattened state on the conveyor belt 73, which is air-permeable and runs over a suction box 44. By suction, the blanks 17 are held in a defined position on the conveyor belt, and the elastic elements 35,36,37,38 in the blanks 17 are prevented from contracting and from gathering the blanks.

As is shown in FIGS. 5 and 6, a folding-and-sealing unit 59 is located overhead of the conveyor belt 73 and comprises gripping means 60,61,62 and 63. In FIG. 5 only gripping means 61 and 63 are visible. The gripping means are brought in contact with the liquid impervious backsheet 23 of the blanks 17 at the four gripping areas 51,53,55 and 57. The gripping means 60–63 are rotatably mounted on carrier arms 64,65,66 and 67. The carrier arms 64–67 are connected to a frame 72 and can each be rotated around at least one hinging axis 75,77. The hinging axes 75,77 extend perpendicular to the plane of the drawing in FIG. 5, and generally perpendicular to the carrier arms 64–67.

As shown in FIG. 6, two sealing means 78,79 are located on each side of the conveyor belt 73 and can be moved in a direction transversely to the direction of transport T to contact an anvil carrier 69. The sealing means 78,79 may comprise heated elements which contact the anvil carrier under pressures of between 1 and $10^5$ psi. Because the anvil carrier 69 is simultaneously contacted by the sealing means 78,79 from both sides and is squeezed between the sealing means, high pressures can be exerted on the side seams without the need for a heavy and rigid suspension of the anvil carrier 69.

Figure 7:
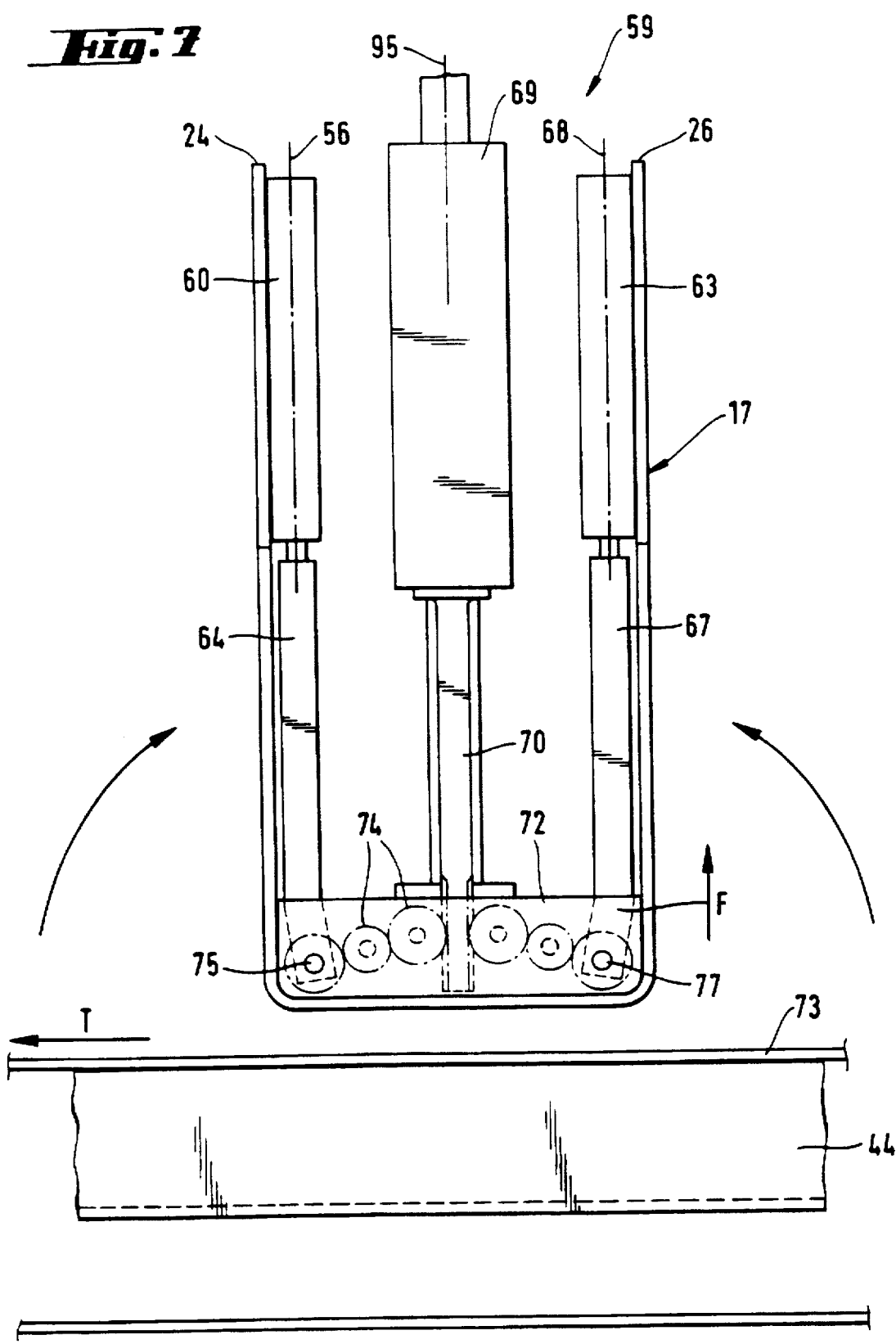
FIGS. 7 and 8 show a side elevational view of the apparatus of FIG. 5 in the sealing position.

The carrier arms 64–67 can be rotated upwardly around the hinging axes 77,75 to a position in which they extend substantially perpendicular to the conveyor belt 73, and such that the sealing areas 43–49 are brought in proximity of the anvil carrier 69. This is illustrated in FIG. 7. The actuating means for rotating the carrier arms 64–69 around the hinge axes 75,77 may for instance be formed by levers or gears or any other known means.

As schematically indicated in FIG. 5, the carrierarm-actuating means for rotating the carrier arms around the hinging axes 75 and 77 may comprise a number of gears 74. The gears 74 for instance engage with a complementary toothed surface on suspension arm 70. By moving the frame 72 along the arm 70 towards the anvil carrier 69, the carrier arms 64–67 are rotated upwardly. The direction of rotation of the carrier arms 64–67 can in this embodiment be easily varied by selecting an even or uneven number of gears in the actuating means. Prior to, or during rotation of the carrier arms, the frame 72 and the anvil carrier 69 may in combination be lifted away from the conveyor belt 73 in the direction of the arrow F towards a sealing position.

In the embodiment FIGS. 5, 6 and 7, the blank 17 is stretched upon rotation of the carrier arms 64–67 around the hinging axes 75, 77. Stretching of the blank can be prevented by hinging the carrier arms 64–67 around hinging axes which lie in the plane of the blank 17. For hinging axes that are not located in the plane of the blank 17 but above the plane of the blank 17, a length compensation is required. To counteract the increase in length of the blank 17 caused by rotating the carrier arms 64–67 upwardly, the folding-and-sealing unit 59 comprises length-compensating means, which may for instance comprise a telescopic arrangement for varying the length of the carrier arms 64–67. In a preferred embodiment, the length-compensating means comprises a suspension of at least one of the hinging axes 75, 77 which causes a varying distance between the hinging axes 75,77 upon rotation of the carrier arms. This is shown in the preferred folding-and-sealing unit 59 of FIGS. 12 and 13.

Figure 8:
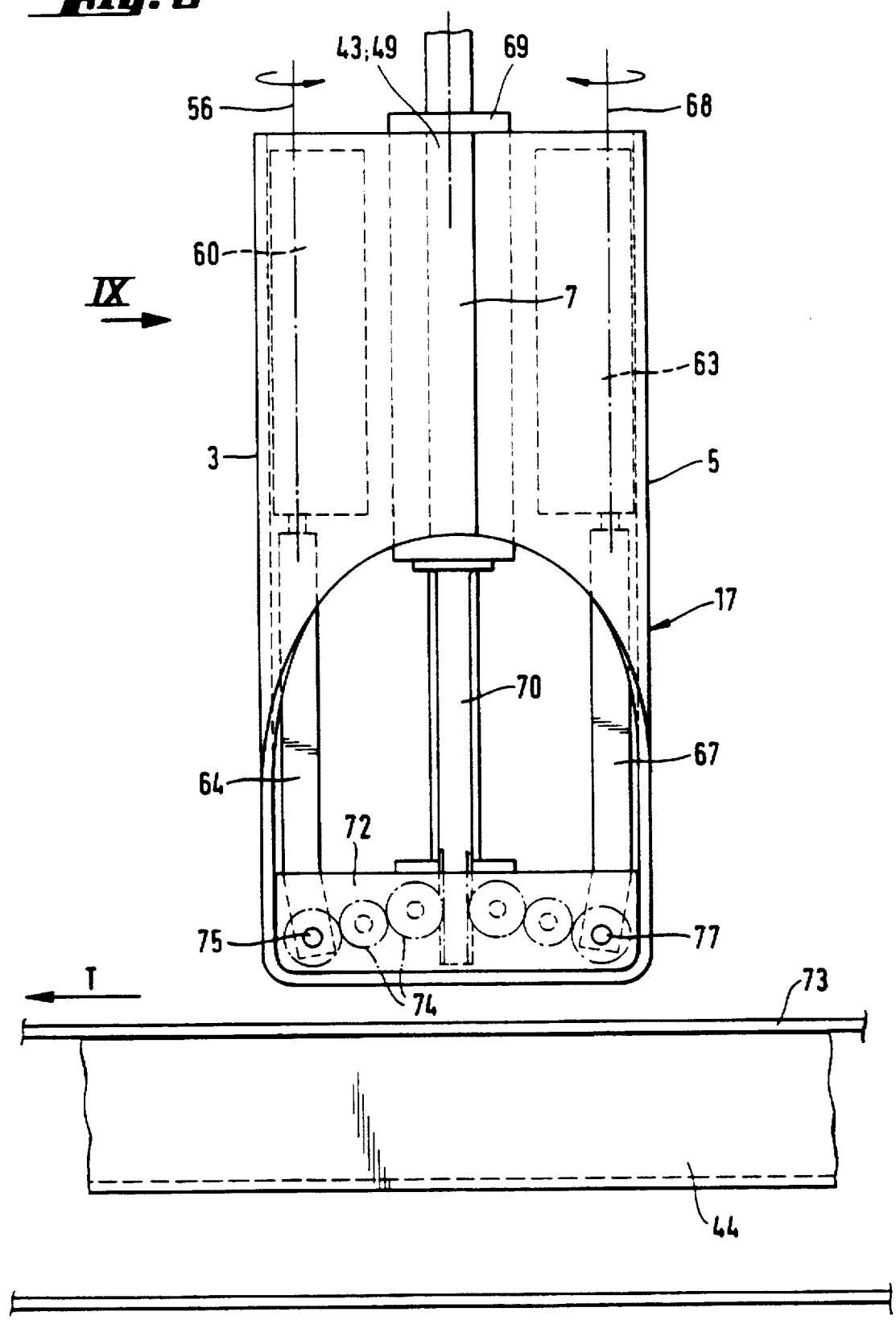

As illustrated in FIG. 8, the sealing areas 45,47 and 43,49, respectively, are placed in an overlapping relationship by rotation of each gripping means 60–63 around a gripper axis 56,56', 68,68' which extend generally parallel to the carrier arms 64–67. The superimposed sealing areas 45,47 and 43,49 are contacted between the anvil carrier 69 and the sealing means 78,79, which may comprise an ultrasonic conductor. The ultrasonic energy imparted to the sealing areas puts the thermoplastic material of the sealing areas in a heat-softened state, such that upon compression of the sealing areas between the anvil and the conductors an overlapping side seam is formed.

Instead of an overlapping seam, in which the sealing areas 43,49 are superimposed generally parallel to the plane of the anvil carrier 69, the gripping means 61,63 may be simultaneously rotated around their gripper axis 56,56'; 68,68' in such a way that the sealing areas 43,49 mutually abutt and extend generally perpendicular to the plane of the anvil carrier 69. Sealing can then occur for instance by compressing the abutting sealing areas 43, 49 in a direction generally parallel to the direction of transport T by sealing means traveling with folding-and-sealing unit 59 at matched speed. Different embodiments of overlapping and abutting side seams are shown in FIGS. 26 to 28.

Figure 9:
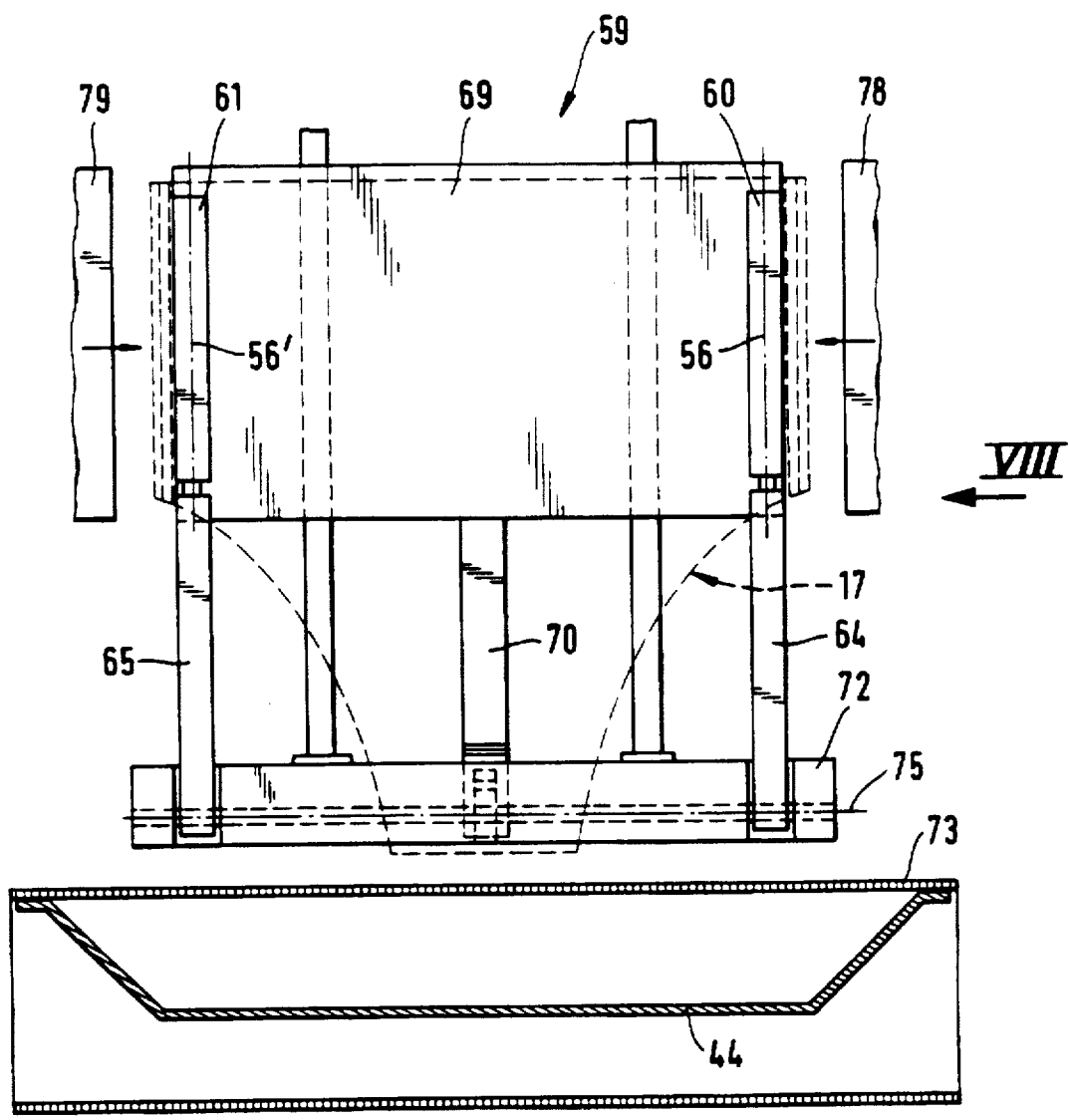
FIG. 9 shows a schematic front elevational view of the apparatus as shown in FIG. 8.

FIG. 9 shows a frontal view of the sealing unit 59 in the sealing position, prior to contacting the ultrasonic conductors 78,79 with the anvil carrier 69. The blank 17 has been indicated by a dashed line. As upon rotation of the gripping means 61,62 around the gripper axes 56,56' the blank 17 is stretched, the mutual distance between the gripping means 61,62 is decreased upon rotation, for instance by displacing the gripping means along the hinging axis 75.

Figure 10:
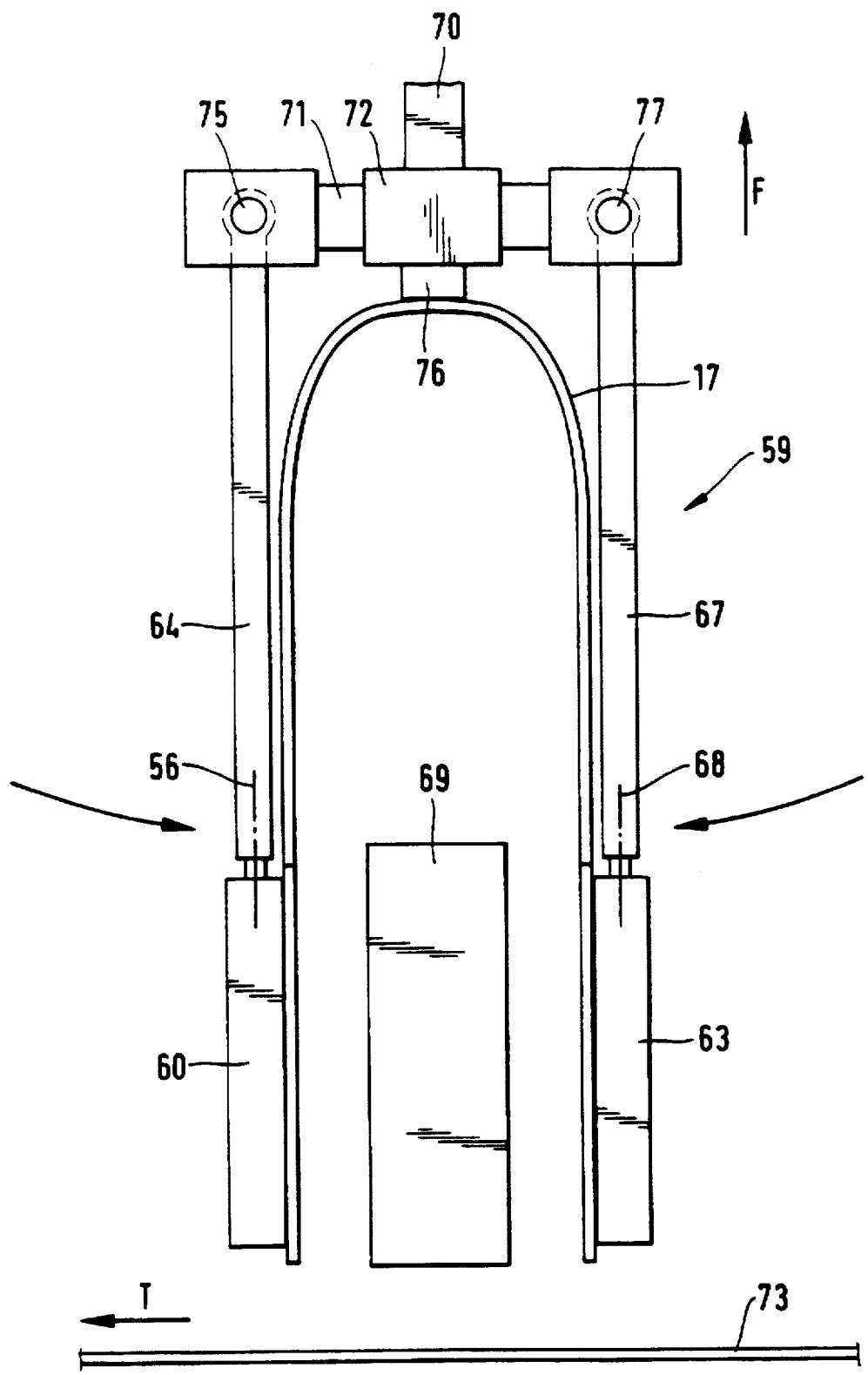
FIG. 10 shows a schematic side elevational view of an embodiment of the apparatus according to the invention in an alternative sealing position.

FIG. 10 shows a schematic side elevational view of a sealing unit, wherein the frame 72 is moved upwards in the direction of the arrow F, and wherein the carrier arms 64–67 are rotated downwardly after gripping the blank 17. In this case the folding of the blank 17 causes an excess of material of the blank 17 to be comprised between the gripping means 61 and 63. To maintain the blank 17 in a tensioned state, the carrier arms 65 and 67 may be moved outwardly along a transverse arm 71. To fix the blank 17 in place during folding, the center point of the blank 17 may be gripped by a gripping means 76 which may comprise for instance a vacuum suction device.

Figure 11:
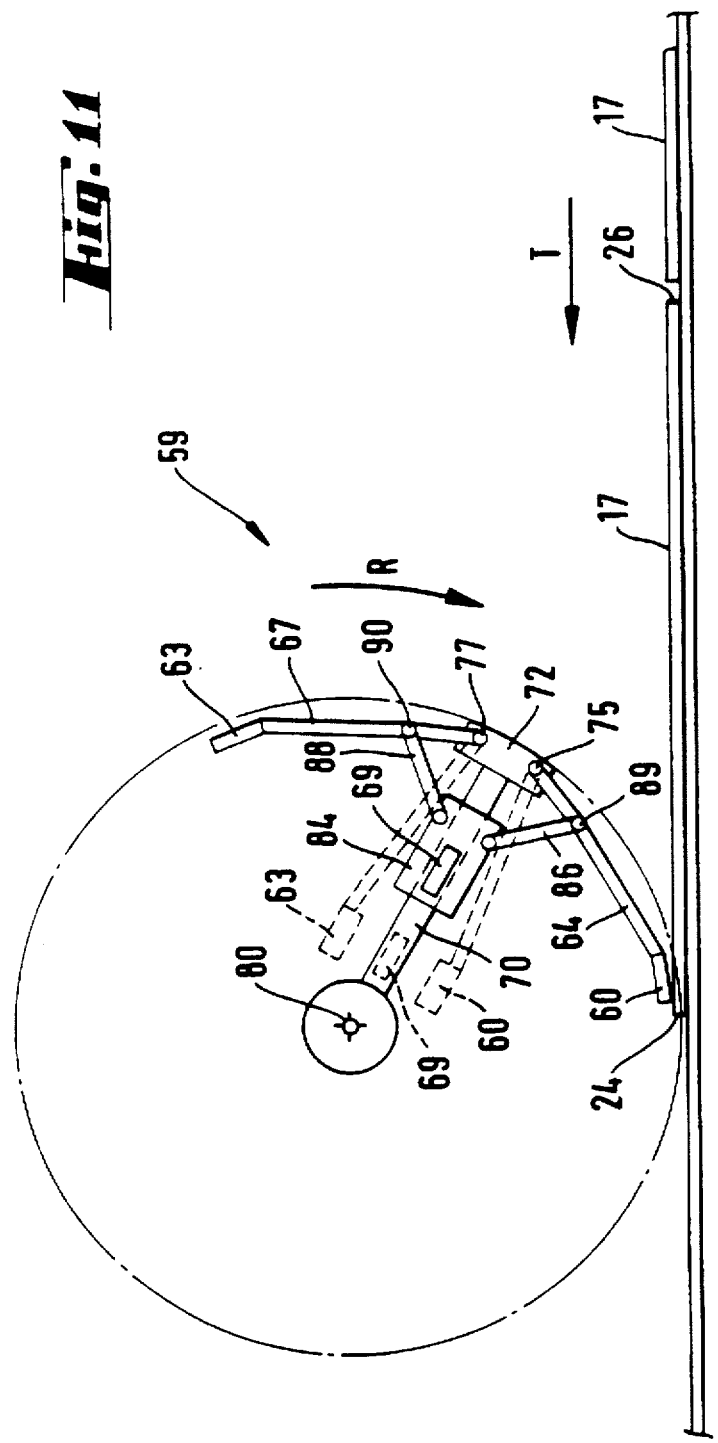
FIG. 11 shows a schematic side elevational view of an embodiment of an umbrella-type apparatus for forming side seams.

FIG. 11 shows a side elevational view of a preferred embodiment of a folding-and-sealing unit 59 for forming side seams at high speed. The carrier arms 64–67 are mounted on the frame 72 which forms an upper member. The frame 72 is mounted on the arm 70, which is rotated around a main axis 80 generally parallel to the hinging axes (75,77) in the direction of the arrow R. The speed of rotation of the arm 70 around the main axis 80 is matched to the speed of transport of the blanks 17, and is such that the circumferential speed of the gripping means 60–63 equals the speed of transport. The leading edge 24 of a blank 17 is gripped by the gripping means 61,62 at a moment when the relative velocity between the blank 17 and the gripping means 61,62 is about zero. The geometry of the foldingand-sealing unit 59 is adapted to the length of the blank 17, and is such that gripping means 60,63 contact the trailing edge 26 of the blank 17 at the moment when the gripping means 60,63 are tangential to the conveyor belt 73.

The carrier-arm actuating means in the embodiment of FIG. 11 comprises a lower member 84 and for each carrier arm a connecting arm 86, 88. The connecting arms 86,88 are connected in hinge points 89,90 to the carrier arms 64–67 and are hingingly connected to the lower member 84. The lower member 84 is slidably mounted on the arm 70 such that the distance between the frame 72 and the lower member 84 can be varied. The carrier arms 64–67 are moved towards the anvil carrier 69, as indicated by the dashed lines, by moving the lower member 84 towards the main axis 80, while keeping the frame 72 stationary with respect to the arm 70. Evidently, it is also possible to move the carrier arms 64–67 to their sealing position by moving the frame 72 along the arm 70 away from a stationary lower member 84. The anvil carrier 69 is mounted on the arm 70 and is rotated together with the carrier arms 64–67.

Figure 12:
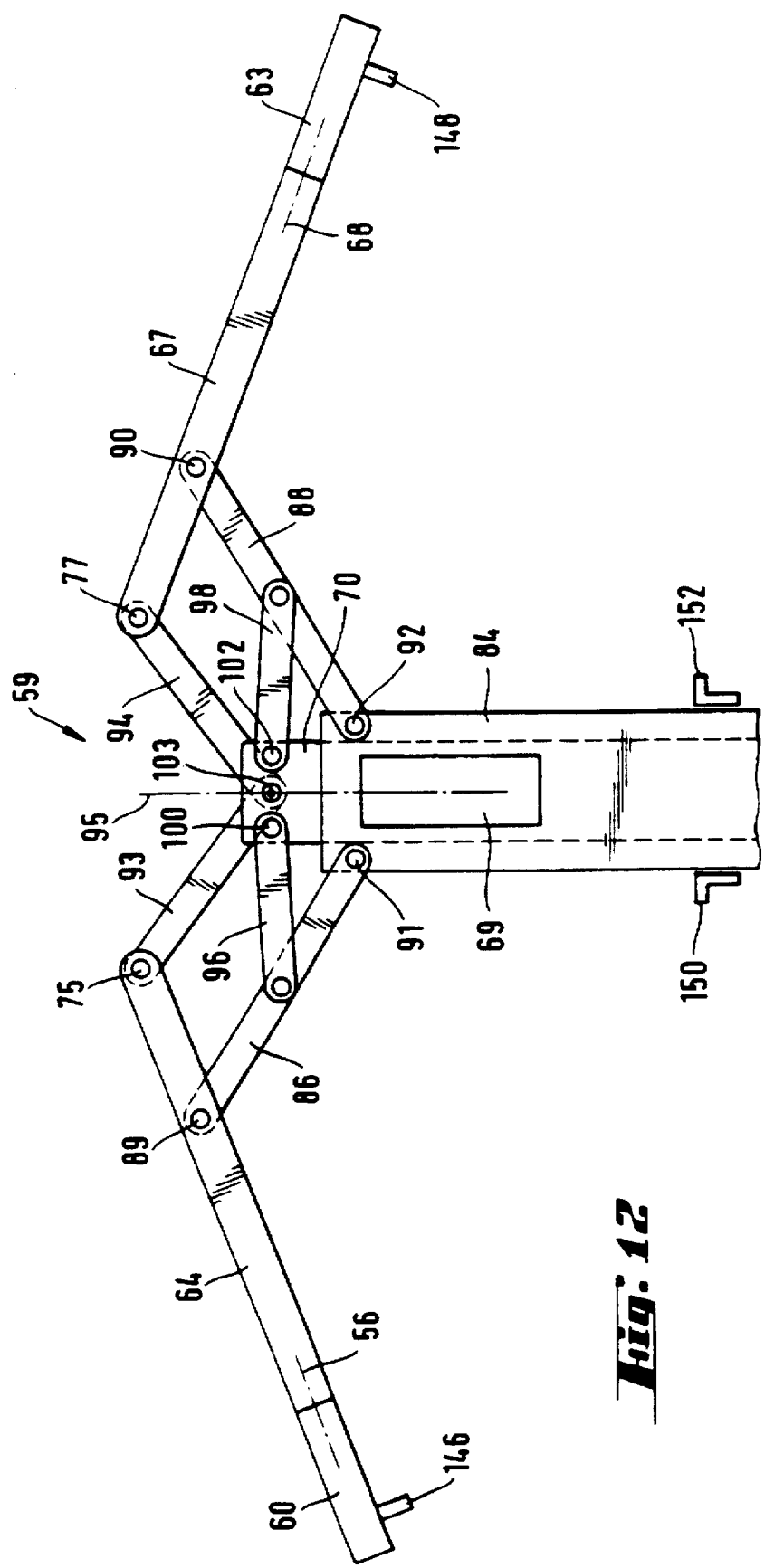
FIG. 12 shows a cross-sectional view of an umbrella-type apparatus for forming side seams in the gripping position.
Figure 13:
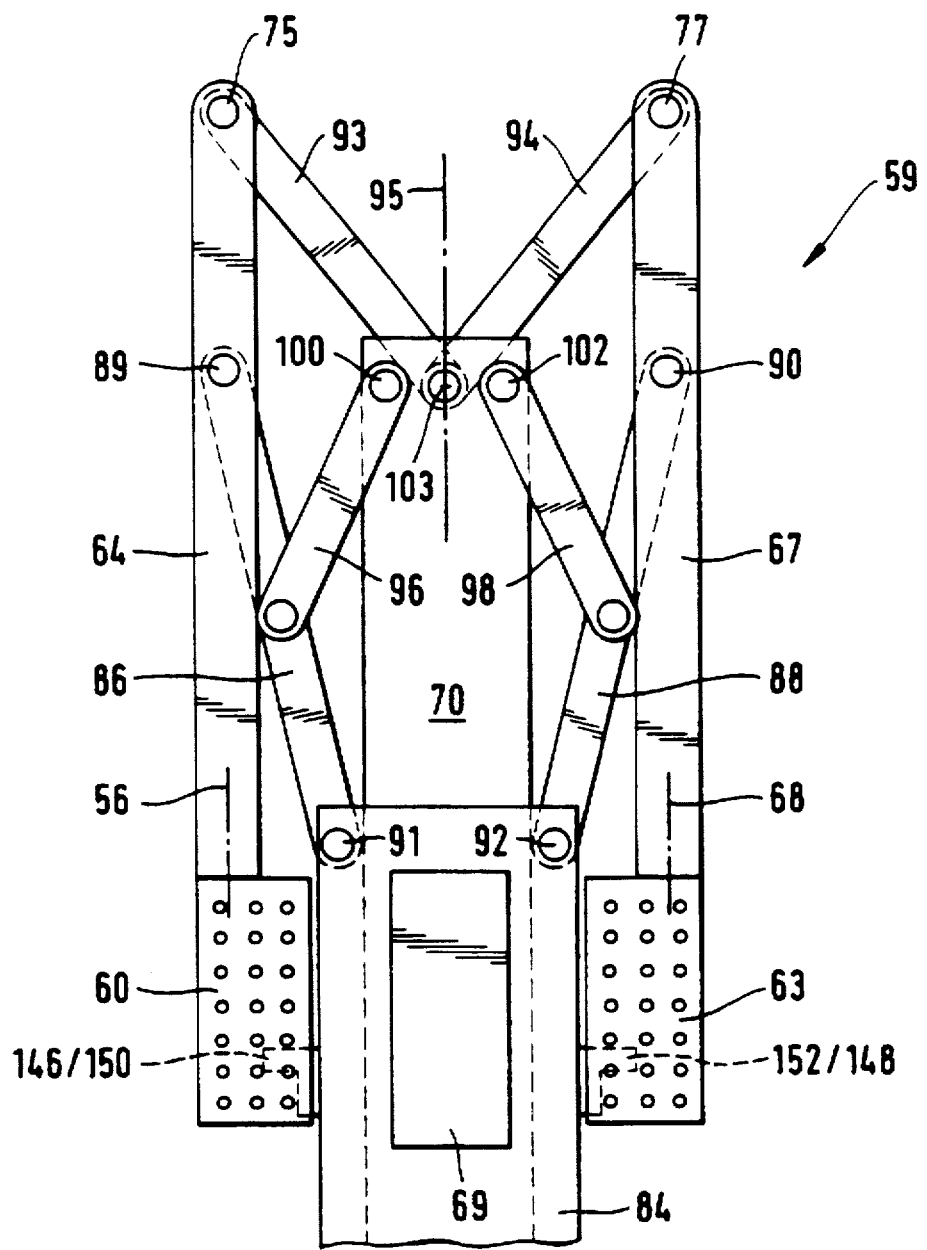
FIG. 13 shows a cross-sectional view of an umbrella-type apparatus for forming side seams in the sealing position.

FIGS. 12 and 13 show detailed cross-sectional views of the folding-and-sealing unit 59 in the gripping phase and in the sealing phase respectively, including the length-compensating means. The length compensating means comprises two pivot arms 93,94 to which the carrier arms 64–67 are connected. The pivot arms 93,94 rotate around a central axis 103, which is connected to the arm 70. By rotation of the pivot arms 93,94 around axis 103, the distance between the hinging axes 75, 77, which extend perpendicular to the plane of the drawing of FIGS. 12 an 13, is varied upon rotation of the carrier arms 64–67.

Furthermore, distance control arms 96, 98 are provided, which are on one side connected to the arm 70 and which have their opposite side attached to the connecting arms 86,88. The distance control arms 96–98 couple the carrier arms 64–67 with the lower member 84 in such a manner that for each position of the lower member 84 along the arm 70, a single position of the carrier arms 65, 67 corresponds.

FIG. 13 shows the lower member 84 in its retracted position wherein the connecting arms 88, 86 have been pulled downwardly generally along the arm 70. The position of the connecting arms 88,86, the distance control arms 96,98 and the pivot members 93,94 is uniquely determined for each position of the carrier arms 65,67. When the connecting arms 86,88 are pulled downwards by the lower member 84, the carrier arms 64–67 are rotated around the hinging axes 75,77, while the hinging axes are moved along a circle segment which is centered on central axis 103.

Figure 14:
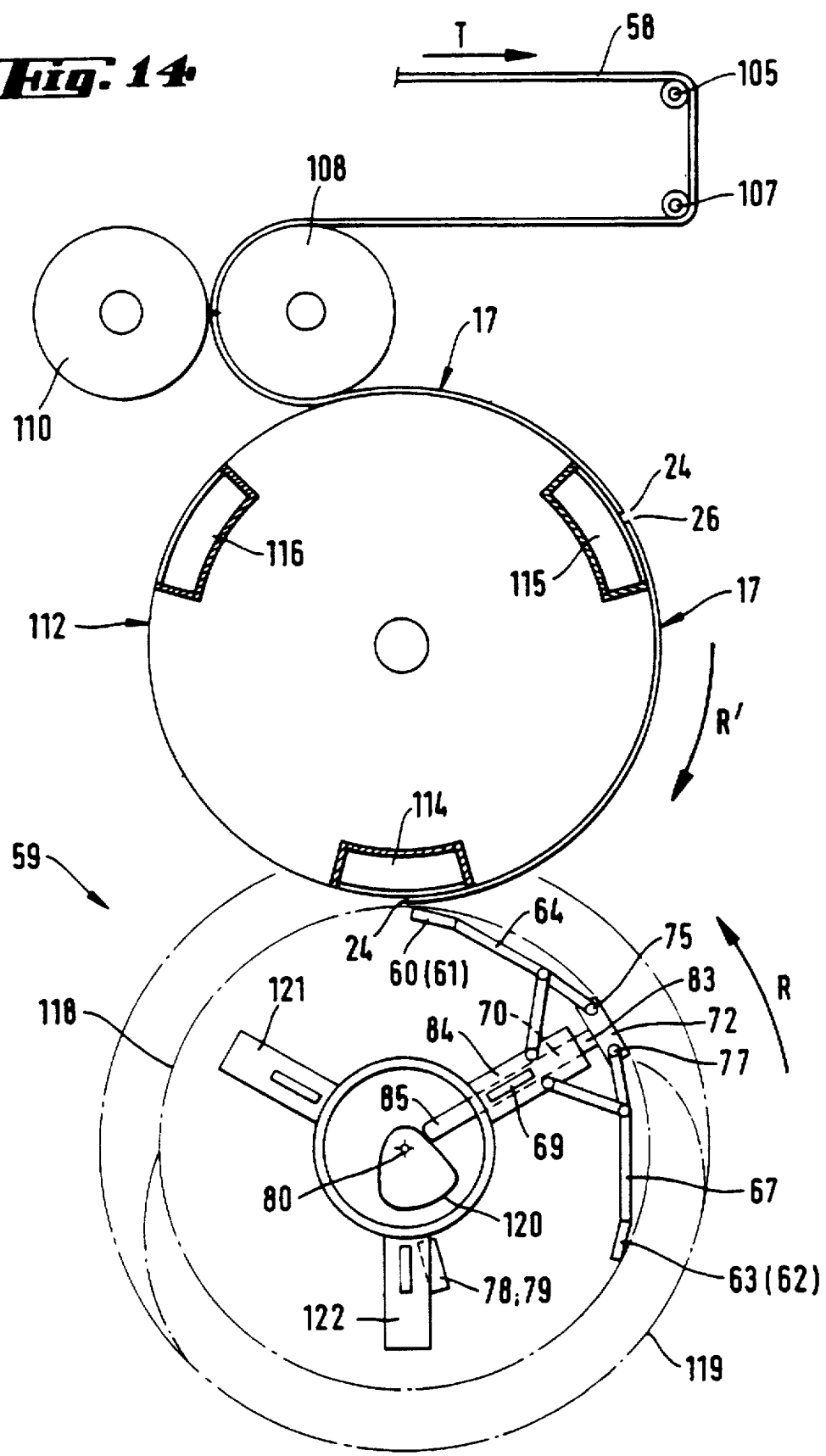
FIGS. 14–17 show schematic side elevational views of the gripping and sealing phases of an umbrella-type apparatus.

FIGS. 14–17 schematically show how from a continuous web 58, individual blanks 17 are cut and how the sealing steps of the sides of the blanks are effected in the preferred embodiment of a folding-and-sealing unit 59 in accordance with the invention. The web 58 is transported along transport means comprising guide rollers 105, 107,108 towards a pick-up drum 112 which is rotated in the direction of the arrow R'. The leading edge 24 of the web 58 is sucked against a vacuum chamber 115 on the periphery of the drum 112, whereas the trailing edge, which in the embodiment of FIG. 14 is formed after cutting of the web in a cutting unit 110, is sucked onto the surface of drum 112 by vacuum chamber 116.

Figure 15:
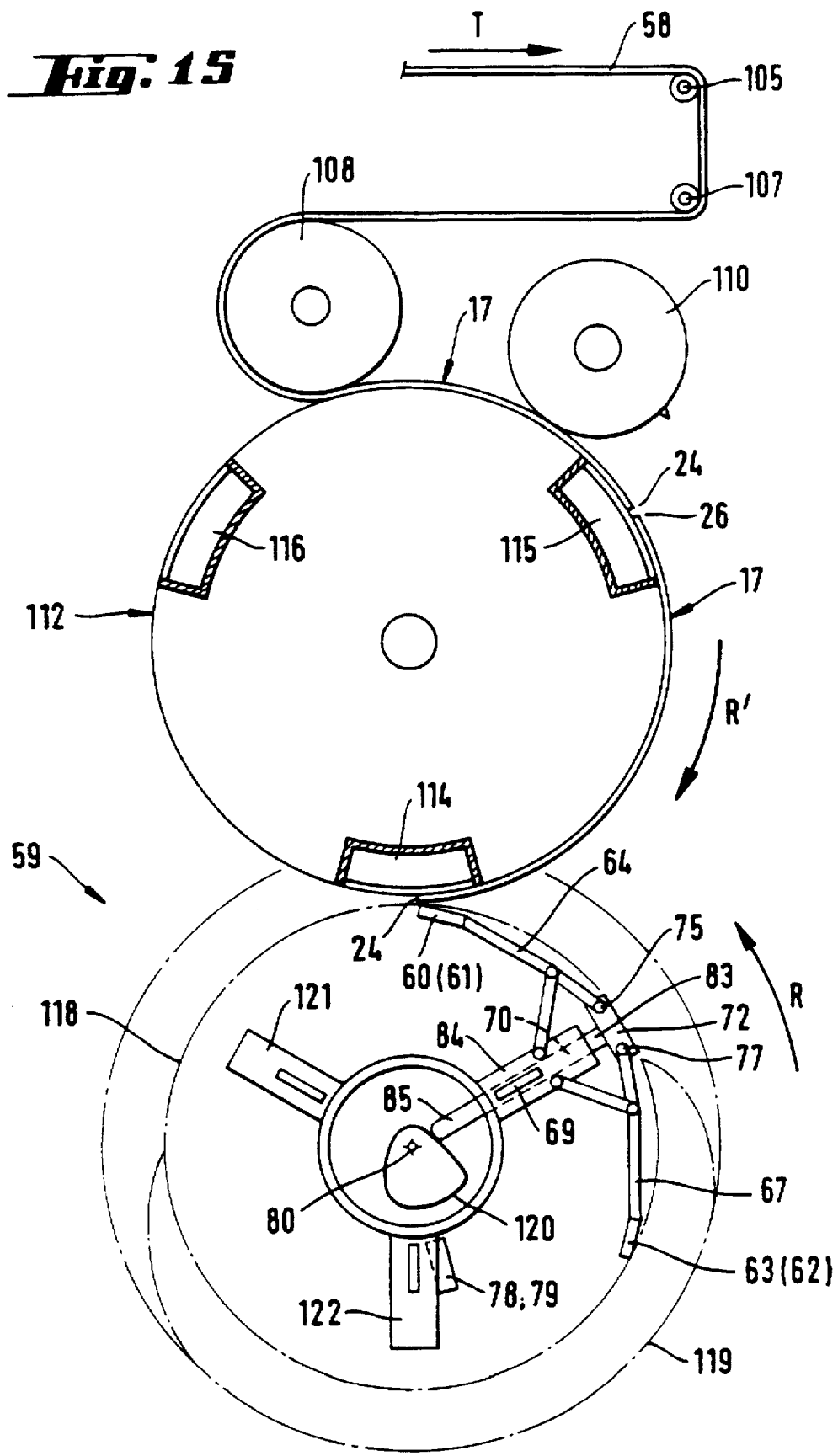

In the embodiment of FIG. 15 the web 58 is first placed across vacuum chambers 115 and 116, and is subsequently cut by cutting unit 110. Placing the cutting unit 110 tangential to the surface of the pick-up drum 112 allows for accurate control of the position of the trailing edge of each blank on the surface of the drum 112.

Figure 16:
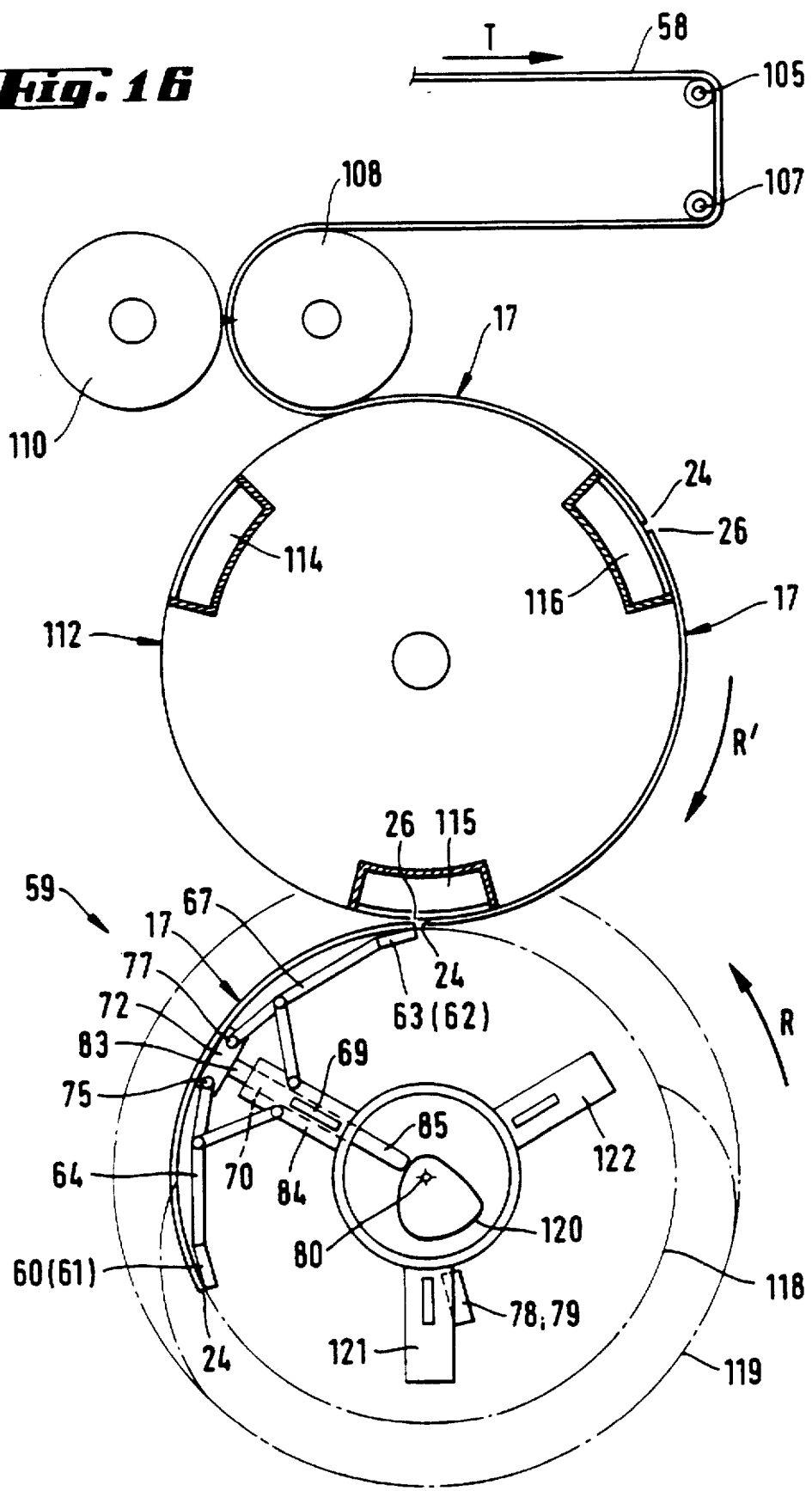

As shown in FIGS. 14 and 15 the gripping means 60, 61, 62 and 63 rotate on a circular track 118 which is tangential to the pick-up drum 112. The leading edge 24 of the pre-form 17 that is held on the drum 112 between the vacuum chamber 114 and 115, is gripped by the gripping means 61 and 62. Subsequently, as shown in FIG. 16, the trailing edge of the blank is gripped by gripping means 60 and 63 from the vacuum chamber 115.

Figure 17:
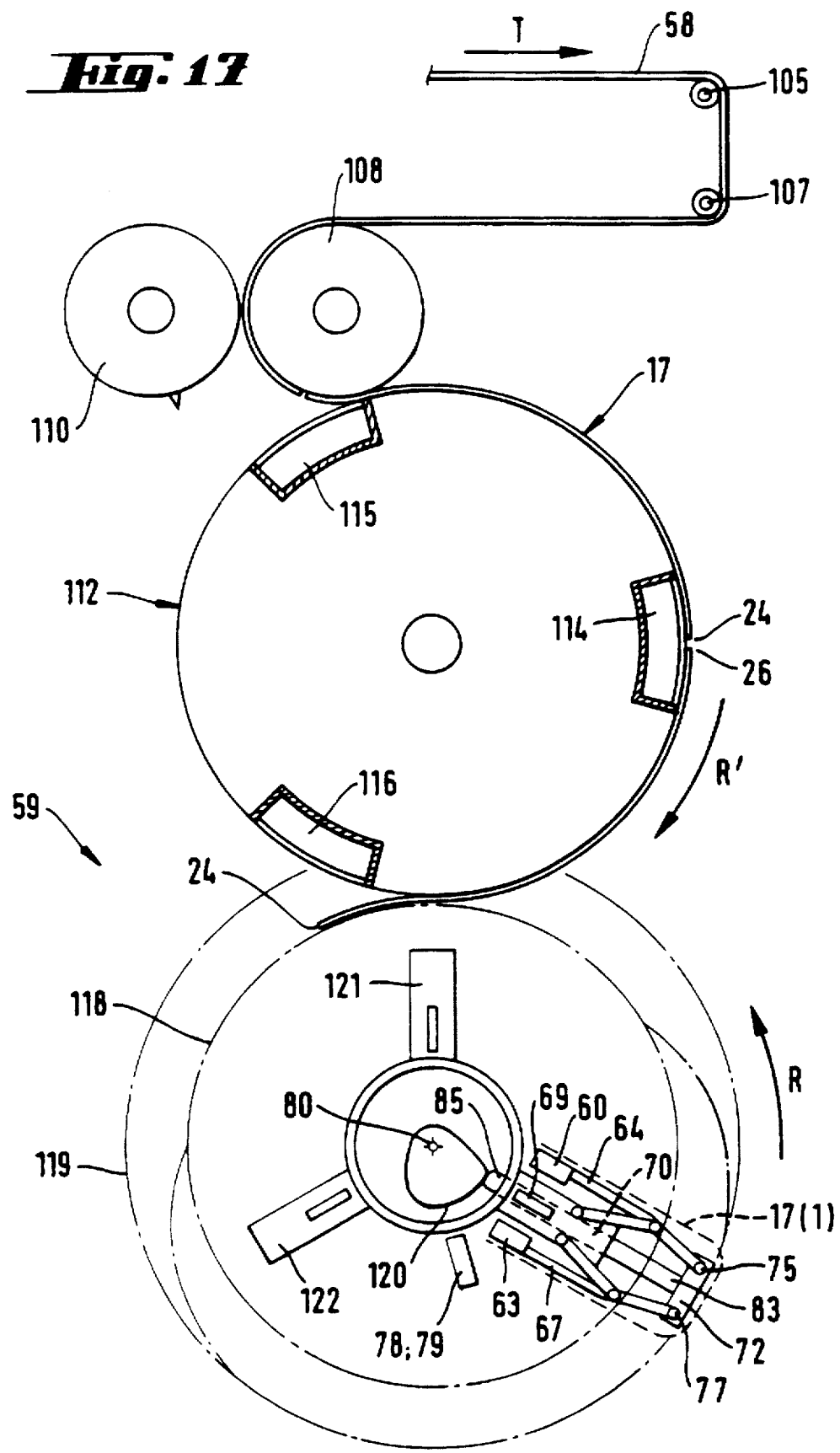

In the embodiment of FIGS. 14–17, the arm 70 of the folding-and-sealing unit 59 comprises an internal telescopic section, having an internal end comprising a cam follower 85 that is to engage a stationary cam surface 120. As shown in FIG. 17, the telescopic section 83 is pressed radially outwardly towards circular track 119 such that the frame 72 is radially displaced and the carrier arms are rotated towards the sealing position.

Inside the telescopic section 83, there may be included a further telescopic element which is to engage a further stationary cam surface, such that after the carrier arms have reached the sealing position, this element is pushed radially outwardly beyond the frame 72 to eject the finished sealed article from the folding-and-sealing unit 59. This construction has not been shown in the figures.

In the embodiment of FIGS. 14–17, a further set of carrier arms is located at each position 121, 122. A single, stationary sealing means 79 such as an ultrasonic conductor is provided along which each set of carrier arms is rotated. For reasons of clarity only a single set of carrier arms has been shown in the FIGS. 14–16. As many as up to 30 identical sets of arms may be located around the main axis 80 to allow sufficient time for the sealing operation while maintaining a high speed of transport of the web 58, which may for instance be transported at speeds of 2 m/s or higher.

In an alternative embodiment, a sealing means 79 is provided for each folding-and-sealing unit at each position 121,122, and rotates with the folding-and-sealing units around the main axis 80. This allows, at a given speed of rotation around the axis 80, for sufficient time of interaction between the sealing means 79 and the material of the pre-form 17. Especially when the sealing means 79 are formed by heat-sealing means, it is important that sufficient time for heating up and cooling down of the side seam material is allowed. In an examplerary embodiment, the heat sealing means 79 require about 700 ms sealing time, which may correspond to a rotation of the sealing means 79 around the axis 80 of about 180 degrees.

Figure 18:
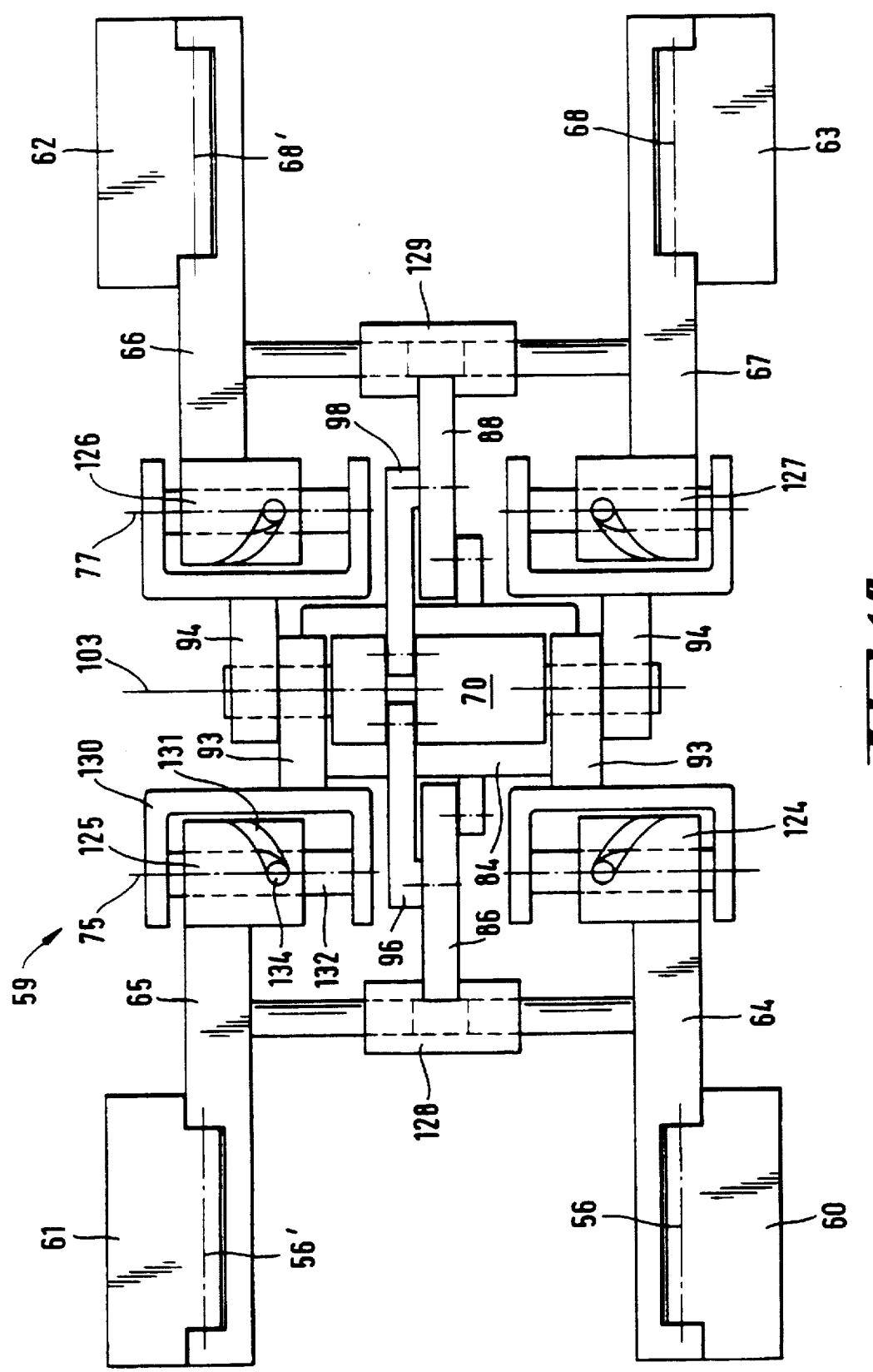
FIG. 18 shows a top cross-sectional view of the umbrella-type apparatus of FIGS. 12 and 13.

FIG. 18 shows a top cross sectional view of the folding-and-sealing unit 59, to more clearly depict the width-compensating means. Each carrier arm 64,65,66 and 67 is connected to a grooved member 124, 125, 126 and 127. Each carrier arm 64–67 is mounted in a sleeve 128, 129 which is part of the pivot members 93,94. The following description is given with respect to gripping means 61, but equally applies to the other gripping means 60, 62 and 63. A grooved member 125 is mounted in a bracket 130, which is connected to the central axis 103 to be jointly rotated with the pivot member 93. The bracket 130 carries an axis 132 generally parallel to the hinging axes (75,77) on which a pin 134 is located which falls in a groove 131 of the member 125. Upon downward rotation of the carrier arm 65 around the hinging axis 75, the grooved member 125 is axially displaced along the axis 132, such that the distance between the gripping means 61 and 62 is decreased.

The gripping means 60–63 are preferably formed by vacuum gripping means. Each vacuum gripping means comprises a hollow body having a plurality of outlets on a gripping surface to contact the gripping areas of the blank. Each hollow body of the gripping members is connected via a flexible vacuum lead to a switched vacuum supply. This has not been indicated in the figures.

As shown in FIGS. 12 and 13, the gripper actuating means for rotation of the gripping means 60–63 around the gripper axes 56,56', 68,68', comprises a protrusion 146,148 on each gripping means and an engaging surface 150,152 mounted on the arm 70. When the carrier arms 64–67 are rotated to the sealing position in which they lie adjacent the arm 70, the protrusions 146,148 are guided along the engaging surfaces 150,152 such that the gripping means are forced to rotate around the gripper axes 56,56', 68,68'.

Figure 19:
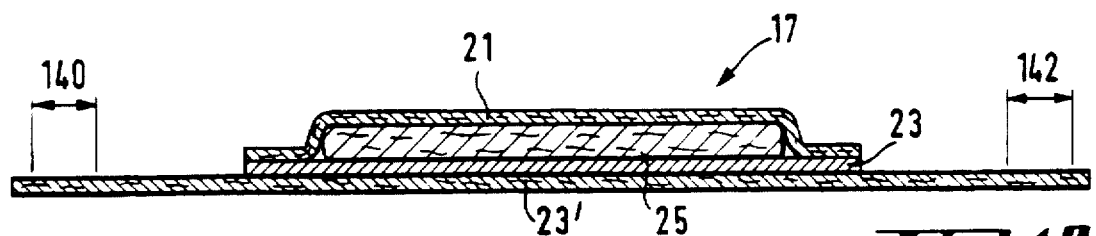
FIGS. 19–23 show cross-sectional views of different embodiment of two-dimensional pre-forms for forming undergarments having side seams.

The FIGS. 19–23 show cross-sectional views of different blanks 17, along a cross-section which extends parallel to the transverse sides of the blanks 17 and which cuts through two sealing areas 140, 142. FIG. 19 shows an embodiment wherein the blank 17 from which the undergarment 1 is formed comprises a topsheet 21, a backsheet 23, 23' and a core 25 interposed between the topsheet and backsheet. The backsheet is formed by a thermoplastic film 23 and a non-woven outer layer 23'. The thermoplastic film 23 is not coterminous with the non-woven outer layer 23' such that in each side seam only two layers of the non-woven material 23' are present. Breathability of the absorbent structure is achieved through the regions of the non-woven material which are not covered by the impermeable film 23.

Figure 20:
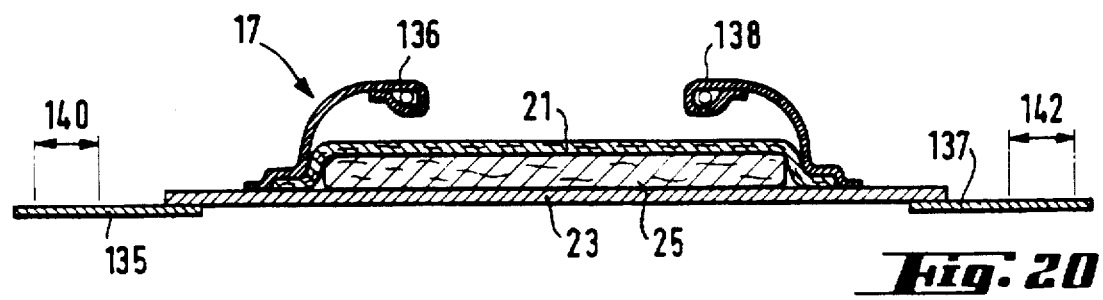

In the embodiment of FIG. 20, the blank 17 comprises a thermoplastic film backsheet 23 having panels 135, 137 of stretchable material attached there-to. Furthermore, there may be provided elasticated stand-up cuffs 136,138 on each side of the core 21.

Figure 21:
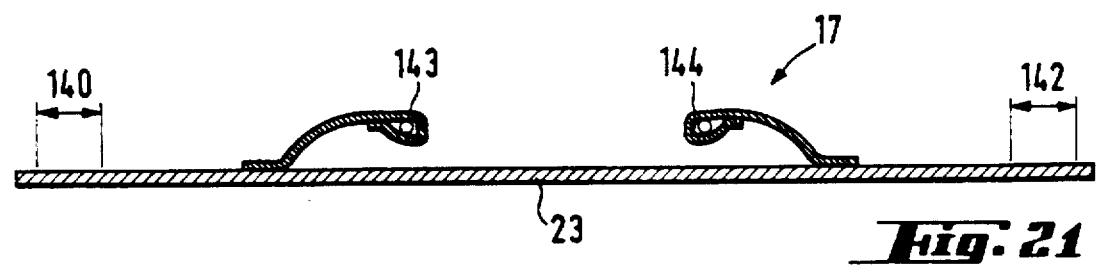

In the embodiment of FIG. 21, the blank 17 is intended to form an undergarment in the form of a re-usable holder for absorbent insert cores, and comprises a non-woven backsheet 23 and two pocket-forming flaps 143,144 in which the disposable insert core can be inserted and which serve to hold the insert core in the proper position with respect to the garment.

Figure 22:
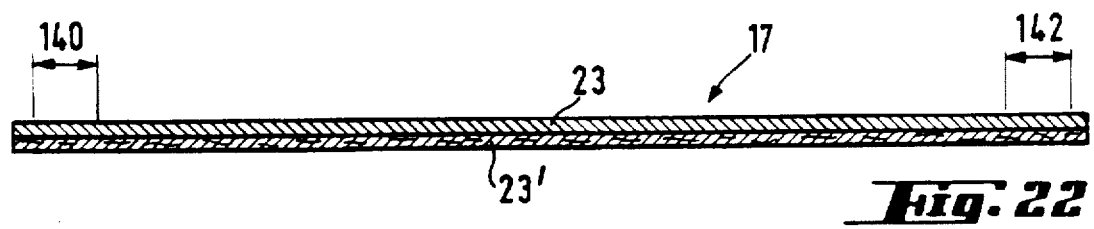

FIG. 22 shows a blank which is made a laminate of two non-woven layers 23,23' or of a nonwoven layer 23' and a thermoplastic layer, both layers extending into the sealing areas 140,142 for improved strength of the seams.

Figure 23:
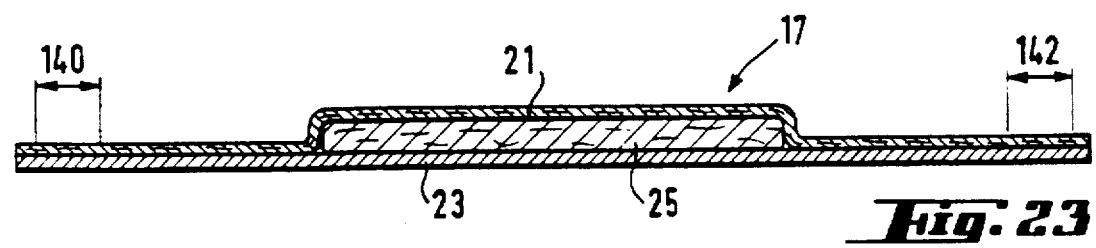

FIG. 23 shows a blank wherein both the topsheet 21 and the backsheet 23 extend into the sealing areas 140, 142 to form reinforced side seams.

While the topsheet 21, the backsheet 23, and the absorbent core 25 may be assembled in a variety of well known configurations, preferred con-figurations are described generally in U.S. Pat. No. 3,860,003 entitled "Contractable Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al. on Sep. 29, 1992; each of which is incorporated herein by reference.

The absorbent core 25 may be any absorbent means which is generally compressible, conformable, non-irritating to the wearer's skin, and capable of absorbing and retaining liquids such as urine and other certain body exudates. The absorbent core 25 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 25 should, however, be compatible with the design loading and the intended use of the absorbent article. Further, the size and absorbent capacity of the absorbent core 25 may be varied to accommodate wearers ranging from infants through adults. Exemplary absorbent structures for use as the absorbent core 25 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference.

The backsheet 23,23' is positioned adjacent the garment surface of the absorbent core 25 and is preferably joined thereto by attachment means (not shown) such as those well known in the art. For example, the backsheet 23 may be secured to the absorbent core 25 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 23 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent core 25 from wetting articles which contact the absorbent articles, such as bedsheets and undergarments. The backsheet 23 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet include RR8220 blown films and RR5475 cast films as manufactured by Tredegar Industries, Inc. of Terre Haute, Ind. The backsheet 23 is preferably embossed and/or matte finished to provide a more clothlike appearance. Further, the backsheet 23 may permit vapors to escape from the absorbent core 25 (i.e., breathable) while still preventing exudates from passing through the backsheet 23.

The topsheet 21 is positioned adjacent the body surface of the absorbent core 25 and is preferably joined thereto and to the backsheet 23 by attachment means (not shown) such as those well known in the art. Suitable attachment means are described with respect to joining the backsheet 23 to the absorbent core 25. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 21 and the backsheet 23 are joined directly to each other in the blank's periphery and are indirectly joined together by directly joining them to the absorbent core 25 by the attachment means (not shown).

The topsheet 21 is compliant, soft feeling, and non-irritating to the wearer's skin. Further, the topsheet 21 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 21 is made of a hydrophobic material to isolate the wearer's skin from liquids contained in the absorbent core 25. There are a number of manufacturing techniques which may be used to manufacture the topsheet 21. For example, the topsheet 21 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The disposable absorbent article preferably further comprises elasticized leg cuffs 36,38; 136,138 for providing improved containment of liquids and other body exudates. Each elasticized leg cuff may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. While each elasticized leg cuff 32 may be configured so as to be similar to any of the leg bands, side flaps, barrier cuffs, or elastic cuffs described above.

The disposable absorbent article preferably further comprises an elastic waist feature 35,37 that provides improved fit and containment. The elastic waist feature is that portion or zone of the absorbent article which is intended to elastically expand and contract to dynamically fit the wearer's waist. The elastic waist feature at least extends longitudinally outwardly from at least one of the waist edges of the absorbent core 25 and generally forms at least a portion of the end edge of the blank 17. Disposable absorbent articles are generally constructed so as to have two elastic waist features 35,37, one positioned in the first waist region and one positioned in the second waist region, although diapers can be constructed with a single elastic waist feature. Further, while the elastic waist feature or any of its constituent elements can comprise a separate element affixed to the absorbent article, the elastic waist feature is preferably constructed as an extension of other elements of the diaper such as the backsheet 23 or the topsheet 21, preferably both the backsheet 23 and the topsheet 21.

The at least one elastic waistband 35,37 may be constructed in a number of different configurations including those described in U.S. Pat. No. 4,515,595 issued to Kievit et al. on May 7, 1985 and the above referenced U.S. Pat. No. 5,151,092; each of these references being incorporated herein by reference.

FIG. 24 shows a top plan view of the web 58, wherein the blanks 17 are oriented with their longitudinal sides in the direction of transport, T, of the web 58. Leg cut-out regions 155 are provided along the longitudinal sides 28,30 of the web 58 and waist elastic elements 35,37 are applied transversely across the web.

In the embodiment of FIG. 25, the blanks 17 are oriented transversely with respect to the web 58, such that the longitudinal sides of the pre-forms 17 correspond to the transverse sides of the web 58. The waist elastic elements 35,37 are applied along and substantially parallel to the longitudinal sides of the web 58 such that they are maintained in an extended state at least during transport of the pre-forms and during the sealing step, the leg cut-out sections 156 extending through a central part of the web 58. In this embodiment, the pre-forms 17 may be rotated by 90°, either prior to, or after gripping by the gripping means 60–63, to align the pre-forms 17 with the direction of transport T.

FIG. 26 shows a schematic top view of the position of the sealing areas 43,49 of the blank 17 upon formation of a butt-type side seam. The sealing means 153,154 compress the sealing areas 43,49 in the direction of the arrows C.

In the embodiment of FIG. 27, a side seam is formed which is a combination of a butt-type seam as shown in FIG. 2 and an overlapping seam as shown in FIG. 1. The seams of FIG. 27 can be obtained by first placing the sealing areas 43,49 in an abutting relationship as shown in FIG. 26, and by subsequently doubling-over of the abutting sealing areas. The doubled-over abutting sealing areas 43,49 are subsequently compressed between the sealing means 79 and the anvil carrier 69. The seam formed in this manner is particularly strong as three layers of material are comprised in the seam.

FIG. 28 shows an overlapping seam in which three layers of material are comprised. In this embodiment, the sealing area 43 is doubled-over before placing it in a superimposed relationship with the sealing area 49. The doubled-over sealing area 43 may be obtained by doubling over one of the longitudinal edges 28,30 of the web 50 before cutting of the individual blanks 17 and adhesively, or by heat-, or ultrasonic sealing, maintain the longitudinal edge in a doubled-over configuration.

What is claimed is:

1. Method of making an undergarment (1) having side seams (7, 9, 16, 18) from a substantially two-dimensional web (58), the web having two longitudinal sides (28, 30) and a first transverse edge (24, 31) extending transversely to the longitudinal sides, the method comprising the steps of:

transporting the web (58) in a substantially flattened position on a transport means (73, 105, 107, 112) along a transport trajectory, cutting the web (58) along a second transverse edge (26, 33) to form a two-dimensional pre-form (17), the pre-form (17) comprising the first and the second transverse edge (24, 31; 26, 33) and two longitudinal edges (27, 29), each longitudinal edge having two waist sections (39, 39'; 41, 41') and a crotch section (40, 40') located intermediate the waist sections, a sealing area (43, 45; 47, 49) being located adjacent and inboard of each waist section, and wherein the longitudinal edges of the pre-form (17) are formed by the transverse edges (24, 31; 26, 33) of the web (58), the transverse edges of the pre-form (17) corresponding to sections of the longitudinal sides (28, 30) of the web (58), gripping the pre-form adjacent each waist section with gripping means (60, 61, 62, 63) in four gripping areas (51, 53, 55, 57), each gripping area being located near a respective sealing area, jointly rotating at least the gripping means which hold the gripping areas in the region of one of the transverse edges around at least one hinging axis (75, 77) extending substantially parallel to the transverse edges (24, 31; 26, 33) of the pre-form (17) to place the transverse edge (24, 31) generally parallel and opposite to the second transverse edge (26, 33), superimposing the sealing areas (43, 49; 45, 47) in a contacting relationship.

joining the superimposed sealing areas in a sealing means (78, 79), thus forming the undergarment, and releasing the undergarment from the gripping means.

2. Method according to claim 1, wherein the step of superimposing the sealing areas comprises rotating each gripping means (60, 61, 62, 63) around a respective axis of rotation (56, 56', 68', 68') extending generally parallel to the longitudinal sides (27, 29) of the pre-form to place the sealing areas in an overlapping relationship to form overlapping side seams (7, 9), or in an abutting relationship to form abutting side seams.

3. Method according to claim 1, comprising the step of forming the web (58) by combining a liquid-impervious backsheet (23, 23'), an absorbent core (25) and a liquid-pervious topsheet (21), such that the undergarment (1) is an absorbent article.

4. Method according to claim 1, wherein after gripping the pre-form (17) in the four gripping areas (51–57), at least one said hinging axis (75, 77) is displaced to prevent stretching the pre-form (17) in the direction of the longitudinal edges (27, 29).

5. Method according to claim 1, wherein after gripping the pre-form (17) in the four gripping areas (51–57), the distance between the gripping areas (51, 53; 55, 57) located along the same transverse edge is decreased to prevent stretching of the pre-form in the direction of the transverse edges (24, 31; 26, 33).

6. Method according to claim 1, wherein the pre-form (17) is rotated towards a stationary sealing means (78, 79) around a main axis (80), which extends generally parallel to said at least one hinging axis (75, 77) of rotation.

7. Method according to claim 6, wherein the gripping means (60,61, 62,63) are rotated tangentially to the transport trajectory.

8. Method according to claim 7, wherein the circumferential velocity of the gripping means (60–63) around the main axis (80) is substantially equal to the speed of transport of the web (58) along the transport trajectory.

9. Method according to claim 1, wherein the gripping means (60–63) comprise suction means.

10. Method according to claim 1, wherein the sealing means (78, 79) is an ultrasonic sealing unit.

11. Method according to claim 1, wherein multiple gripping means (60–63, 121–122) are mounted around the main axis (80).

12. Method according to claim 1, wherein the pre-form (17) comprises at least one elastic waist element (35, 37) extending substantially parallel to a transverse edge (24, 31; 26, 33), wherein the method comprises maintaining the at least one said elastic waist element in an extended state at least during transport of the pre-form and during the sealing step.

13. Method according to claim 12 wherein the pre-form (17) comprises at least one said elastic waist element (35, 37) along each transverse edge (24, 31; 26, 33).

14. An apparatus for making an undergarment (1) having side seams (7, 9, 16, 18) from a substantially two-dimensional web (58), the web laving two longitudinal sides (28, 30) and a first transverse edge (24, 31) extending transversely to the longitudinal sides, the web being transported along a transport trajectory and cut along a second transverse edge (26, 33) to form a two-dimensional pre-form (17), the pre-form comprising the first and second transverse edge (24, 31; 26, 33) and two longitudinal edges (27, 29), each longitudinal edge having two waist sections (39, 39'; 41, 41') and a crotch section (40, 40') located intermediate the waist sections, a sealing area (43, 45; 47, 49) being located adjacent and inboard of each waist section, the apparatus comprising at least one folding-and-sealing unit (59), each folding-and-sealing unit (59) having a frame (72) and comprising:

a) at least a first and second carrier arm (64, 65, 66, 67), each carrier arm being connected to the frame (72) and mounted on a hinging axis (75, 77) extending generally transversely to the carrier arms and substantially parallel to the transverse edges (24, 31; 26, 33) of the pre-form (17), b) gripping means (60, 61, 62, 63) attached to each carrier arm for gripping the pre-form (17) in four gripping areas (51, 53, 55, 57), each gripping area being located near a respective sealing area, c) carrier arm-actuating means (70, 74, 84, 86, 88) for rotating at least the carrier arm with the gripping means holding the gripping areas in the region of one of the transverse edges around its hinging axis to a sealing position, said carrier arm-actuating means having a lower member (84), and d) sealing means (78, 79) for contacting the pre-form in the sealing areas when the carrier arms and gripping means are in the sealing position.

15. The apparatus according to claim 14, wherein the gripping means (60, 61, 62, 63) are rotatable around a respective gripper axis (56, 56', 68, 68') which is positioned generally parallel to the carrier arms (64–67), the apparatus comprising gripper actuating means (146, 148, 150, 152) for rotating each gripping means around the gripper axes to a sealing position.

16. The apparatus according to claim 14, the carrier arm-actuating means comprising:
   at least two connecting arms (86, 88) having a pair of hinge points, each said connecting arm being rotatably attached to one of said carrier arms at one hinge point (89, 90) and attached to said lower member (84) of said carrier arm-actuating means at said other hinge point (91, 92), the carrier arm-actuating means being adapted to periodically vary the distance between the hinging axes (75, 77) and the hinge points (91, 92) attaching the connecting arms to the lower member.

17. The apparatus according to claim 16, the hinging axes (75, 77) being located in the frame (72), the lower member (84) being displaceable relative to the frame (72) along a center line (95) located midway between the hinging axes (75, 77) and extending generally transversely to the hinging axes.

18. The apparatus according to claim 17, wherein each carrier arm (64–67) is connected with its hinging axes (75, 77) to a first end of a respective pivot member (93, 94), the second end of each pivot member being rotatably connected to a central pivot axis (103) located on the center line (95) and extending generally parallel to the hinging axes (75, 77).

19. The apparatus according to claim 18, wherein the apparatus comprises two distance-control arms (96,98) each distance-control arm being with one end hingingly connected to a respective connecting arm (86,88) and being with another end hingingly connected to a respective hinge point (100,102) in the region of the center line (95).

20. The apparatus according to claim 18, comprising a sealing anvil (69) being connected to the lower member (84) on the center line (95), each said carrier arm (64–67) being in the sealing position located on each side of the sealing anvil (69).

21. The apparatus according to claim 14, wherein two gripping means (60–63) are connected to each carrier arm, the apparatus further comprising width-compensating means (128, 129, 124, 125, 126, 127) for moving the gripping means (60–63) that are located on the same carrier arm in opposite directions generally parallel to the hinging axes (75, 77).

22. The apparatus according to claim 14, wherein the folding-and-sealing unit (59) is rotatable around a main axis (80) which is generally parallel to the hinging axes (75, 77).

23. The apparatus according to claim 22, wherein a plurality of folding-and-sealing units (59, 121, 122) is mounted at spaced apart angular positions around the main axis (80).

24. The apparatus according to claim 22, wherein the carrier arms (64–67) are rotatable around the main axis (80) at the same circumferential velocity as the speed of transport of the web (58).

25. The apparatus according to claim 14 wherein the frame (72) or the lower member (84) comprises a cam follower (85) that engages and rotates relative to a cam surface (120), for varying the distance between the frame and the lower member.

26. The apparatus according to claim 14, wherein the gripping means (60–63) comprise vacuum gripper means.

27. The apparatus according to claim 14, comprising an ejection member for radially discarding the undergarment after sealing of the sealing areas.

* * * * *